US012758776B2

(12) United States Patent
Malekmohammadi et al.

(10) Patent No.: US 12,758,776 B2
(45) Date of Patent: Oct. 13, 2026

(54) SYSTEMS AND METHODS FOR USING COST PARAMETERS FOR PROGRAMMING ELECTRICAL STIMULATION

(71) Applicant: Boston Scientific Neuromodulation Corporation, Valencia, CA (US)

(72) Inventors: Mahsa Malekmohammadi, Sherman Oaks, CA (US); Richard Mustakos, Simi Valley, CA (US); Leon Mauricio Juarez Paz, Berlin (DE); Lisa Denise Moore, Glendale, CA (US); Stephen Carcieri, Los Angeles, CA (US); Stephen Randolph Smith, III, North Hollywood, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 890 days.

(21) Appl. No.: 18/110,151

(22) Filed: Feb. 15, 2023

(65) Prior Publication Data

US 2023/0264025 A1 Aug. 24, 2023

Related U.S. Application Data

(60) Provisional application No. 63/320,176, filed on Mar. 15, 2022, provisional application No. 63/313,710, filed on Feb. 24, 2022.

(51) Int. Cl.
*A61N 1/36* (2006.01)

(52) U.S. Cl.
CPC ..... *A61N 1/36132* (2013.01); *A61N 1/36146* (2013.01)

(58) Field of Classification Search
CPC ............ A61N 1/37235; A61N 1/37247; A61N 1/36146; A61N 1/36142; A61N 1/3615
See application file for complete search history.

(56) References Cited

U.S. PATENT DOCUMENTS

| | | | |
|---|---|---|---|
| 3,999,555 | A | 12/1976 | Person |
| 4,144,889 | A | 3/1979 | Tyers et al. |

(Continued)

FOREIGN PATENT DOCUMENTS

| | | |
|---|---|---|
| EP | 0813889 | 12/1997 |
| EP | 1048320 | 11/2000 |

(Continued)

OTHER PUBLICATIONS

Butson et al., "Tissue and Electrode Capacitance Reduce Neural Activation Volumes During Deep Brain Stimulation", Clinical Neurophysiology, 116:2490-2500, Oct. 2005.

(Continued)

*Primary Examiner* — George R Evanisko
(74) *Attorney, Agent, or Firm* — Branch Partners PLLC; Bruce E. Black

(57) ABSTRACT

A method for programming an electrical stimulation system including at least one implantable electrical stimulation lead including a plurality of electrodes that includes receiving a target and a location of the at least one implantable electrical stimulation lead; receiving at least one stimulation criterion; for each of the at least one stimulation criterion, identifying one or more values of a cost parameter that meet the stimulation criterion, wherein the cost parameter includes a ratio of a cost of stimulating at least one defined region of tissue over a benefit of stimulating a region of the target; and providing at least one of the one or more values of the cost parameter that meet the at least one stimulation criterion to a user or the electrical stimulation system to assist in programming the electrical stimulation system.

20 Claims, 7 Drawing Sheets

(56) References Cited

U.S. PATENT DOCUMENTS

| | | | |
|---|---|---|---|
| 4,177,818 | A | 12/1979 | De Pedro |
| 4,341,221 | A | 7/1982 | Testerman |
| 4,378,797 | A | 4/1983 | Osterholm |
| 4,445,500 | A | 5/1984 | Osterholm |
| 4,735,208 | A | 4/1988 | Wyler et al. |
| 4,765,341 | A | 8/1988 | Mower et al. |
| 4,841,973 | A | 6/1989 | Stecker |
| 5,067,495 | A | 11/1991 | Brehm |
| 5,099,846 | A | 3/1992 | Hardy |
| 5,222,494 | A | 6/1993 | Baker, Jr. |
| 5,255,693 | A | 10/1993 | Dutcher |
| 5,259,387 | A | 11/1993 | dePinto |
| 5,304,206 | A | 4/1994 | Baker et al. |
| 5,344,438 | A | 9/1994 | Testerman et al. |
| 5,361,763 | A | 11/1994 | Kao et al. |
| 5,452,407 | A | 9/1995 | Crook |
| 5,560,360 | A | 10/1996 | Filler et al. |
| 5,565,949 | A | 10/1996 | Kasha, Jr. |
| 5,593,427 | A | 1/1997 | Gliner et al. |
| 5,601,612 | A | 2/1997 | Gliner et al. |
| 5,607,454 | A | 3/1997 | Cameron et al. |
| 5,620,470 | A | 4/1997 | Gliner et al. |
| 5,651,767 | A | 7/1997 | Schulman |
| 5,711,316 | A | 1/1998 | Elsberry et al. |
| 5,713,922 | A | 2/1998 | King |
| 5,716,377 | A | 2/1998 | Rise et al. |
| 5,724,985 | A | 3/1998 | Snell et al. |
| 5,749,904 | A | 5/1998 | Gliner et al. |
| 5,749,905 | A | 5/1998 | Gliner et al. |
| 5,776,170 | A | 7/1998 | MacDonald et al. |
| 5,782,762 | A | 7/1998 | Vining |
| 5,843,148 | A | 12/1998 | Gijsbers et al. |
| 5,859,922 | A | 1/1999 | Hoffmann |
| 5,868,740 | A | 2/1999 | LeVeen et al. |
| 5,897,583 | A | 4/1999 | Meyer et al. |
| 5,910,804 | A | 6/1999 | Fortenbery et al. |
| 5,925,070 | A | 7/1999 | King et al. |
| 5,938,688 | A | 8/1999 | Schiff |
| 5,938,690 | A | 8/1999 | Aw et al. |
| 5,978,713 | A | 11/1999 | Prutchi et al. |
| 6,016,449 | A | 1/2000 | Fischell et al. |
| 6,029,090 | A | 2/2000 | Herbst |
| 6,029,091 | A | 2/2000 | de la Rama et al. |
| 6,050,992 | A | 4/2000 | Nichols |
| 6,058,331 | A | 5/2000 | King |
| 6,066,163 | A | 5/2000 | John |
| 6,080,187 | A | 6/2000 | Alt et al. |
| 6,083,162 | A | 7/2000 | Vining |
| 6,094,598 | A | 7/2000 | Elsberry et al. |
| 6,096,756 | A | 8/2000 | Crain et al. |
| 6,106,460 | A | 8/2000 | Panescu et al. |
| 6,109,269 | A | 8/2000 | Rise et al. |
| 6,128,538 | A | 10/2000 | Fischell et al. |
| 6,129,685 | A | 10/2000 | Howard, III |
| 6,146,390 | A | 11/2000 | Heilbrun et al. |
| 6,161,044 | A | 12/2000 | Silverstone |
| 6,167,311 | A | 12/2000 | Rezai |
| 6,181,969 | B1 | 1/2001 | Gord |
| 6,192,266 | B1 | 2/2001 | Dupree et al. |
| 6,205,361 | B1 | 3/2001 | Kuzma |
| 6,208,881 | B1 | 3/2001 | Champeau |
| 6,240,308 | B1 | 5/2001 | Hardy et al. |
| 6,246,912 | B1 | 6/2001 | Sluijter et al. |
| 6,253,109 | B1 | 6/2001 | Gielen |
| 6,289,239 | B1 | 9/2001 | Panescu et al. |
| 6,301,492 | B1 | 10/2001 | Zonenshayn |
| 6,310,619 | B1 | 10/2001 | Rice |
| 6,319,241 | B1 | 11/2001 | King |
| 6,336,899 | B1 | 1/2002 | Yamazaki |
| 6,343,226 | B1 | 1/2002 | Sunde et al. |
| 6,351,675 | B1 | 2/2002 | Tholen et al. |
| 6,353,762 | B1 | 3/2002 | Baudino et al. |
| 6,366,813 | B1 | 4/2002 | Dilorenzo |
| 6,368,331 | B1 | 4/2002 | Front et al. |
| 6,389,311 | B1 | 5/2002 | Whayne et al. |
| 6,393,325 | B1 | 5/2002 | Mann et al. |
| 6,421,566 | B1 | 7/2002 | Holsheimer |
| 6,435,878 | B1 | 8/2002 | Reynolds et al. |
| 6,442,432 | B2 | 8/2002 | Lee |
| 6,463,328 | B1 | 10/2002 | John |
| 6,491,699 | B1 | 12/2002 | Henderson et al. |
| 6,494,831 | B1 | 12/2002 | Koritzinsky |
| 6,507,759 | B1 | 1/2003 | Prutchi et al. |
| 6,510,347 | B2 | 1/2003 | Borkan |
| 6,516,227 | B1 | 2/2003 | Meadows et al. |
| 6,517,480 | B1 | 2/2003 | Krass |
| 6,539,263 | B1 | 3/2003 | Schiff |
| 6,560,490 | B2 | 5/2003 | Grill et al. |
| 6,579,280 | B1 | 6/2003 | Kovach et al. |
| 6,600,956 | B2 | 7/2003 | Maschino et al. |
| 6,606,523 | B1 | 8/2003 | Jenkins |
| 6,609,029 | B1 | 8/2003 | Mann et al. |
| 6,609,031 | B1 | 8/2003 | Law et al. |
| 6,609,032 | B1 | 8/2003 | Woods et al. |
| 6,622,048 | B1 | 9/2003 | Mann et al. |
| 6,631,297 | B1 | 10/2003 | Mo |
| 6,654,642 | B2 | 11/2003 | North et al. |
| 6,662,053 | B2 | 12/2003 | Borkan |
| 6,675,046 | B2 | 1/2004 | Holsheimer |
| 6,684,106 | B2 | 1/2004 | Herbst |
| 6,687,392 | B1 | 2/2004 | Touzawa et al. |
| 6,690,972 | B2 | 2/2004 | Conley et al. |
| 6,690,974 | B2 | 2/2004 | Archer et al. |
| 6,692,315 | B1 | 2/2004 | Soumillion et al. |
| 6,694,162 | B2 | 2/2004 | Hartlep |
| 6,694,163 | B1 | 2/2004 | Vining |
| 6,708,096 | B1 | 3/2004 | Frei et al. |
| 6,741,892 | B1 | 5/2004 | Meadows et al. |
| 6,748,098 | B1 | 6/2004 | Rosenfeld |
| 6,748,276 | B1 | 6/2004 | Daignault, Jr. et al. |
| 6,778,846 | B1 | 8/2004 | Martinez et al. |
| 6,788,969 | B2 | 9/2004 | Dupree et al. |
| 6,795,737 | B2 | 9/2004 | Gielen et al. |
| 6,827,681 | B2 | 12/2004 | Tanner et al. |
| 6,830,544 | B2 | 12/2004 | Tanner |
| 6,845,267 | B2 | 1/2005 | Harrison et al. |
| 6,850,802 | B2 | 2/2005 | Holsheimer |
| 6,895,280 | B2 | 5/2005 | Meadows et al. |
| 6,909,913 | B2 | 6/2005 | Vining |
| 6,937,891 | B2 | 8/2005 | Leinders et al. |
| 6,937,903 | B2 | 8/2005 | Schuler et al. |
| 6,944,497 | B2 | 9/2005 | Stypulkowski |
| 6,944,501 | B1 | 9/2005 | Pless |
| 6,950,707 | B2 | 9/2005 | Whitehurst |
| 6,969,388 | B2 | 11/2005 | Goldman et al. |
| 6,993,384 | B2 | 1/2006 | Bradley et al. |
| 7,003,349 | B1 | 2/2006 | Andersson et al. |
| 7,003,352 | B1 | 2/2006 | Whitehurst |
| 7,008,370 | B2 | 3/2006 | Tanner et al. |
| 7,008,413 | B2 | 3/2006 | Kovach et al. |
| 7,035,690 | B2 | 4/2006 | Goetz |
| 7,043,293 | B1 | 5/2006 | Baura |
| 7,047,082 | B1 | 5/2006 | Schrom et al. |
| 7,047,084 | B2 | 5/2006 | Erickson et al. |
| 7,050,857 | B2 | 5/2006 | Samuelsson et al. |
| 7,054,692 | B1 | 5/2006 | Whitehurst et al. |
| 7,058,446 | B2 | 6/2006 | Schuler et al. |
| 7,082,333 | B1 | 7/2006 | Bauhahn et al. |
| 7,107,102 | B2 | 9/2006 | Daignault et al. |
| 7,126,000 | B2 | 10/2006 | Ogawa et al. |
| 7,127,297 | B2 | 10/2006 | Law et al. |
| 7,136,518 | B2 | 11/2006 | Griffin et al. |
| 7,136,695 | B2 | 11/2006 | Pless et al. |
| 7,142,923 | B2 | 11/2006 | North et al. |
| 7,146,219 | B2 | 12/2006 | Sieracki et al. |
| 7,146,223 | B1 | 12/2006 | King |
| 7,151,961 | B1 | 12/2006 | Whitehurst |
| 7,155,279 | B2 | 12/2006 | Whitehurst |
| 7,167,760 | B2 | 1/2007 | Dawant et al. |
| 7,177,674 | B2 | 2/2007 | Echauz et al. |
| 7,181,286 | B2 | 2/2007 | Sieracki et al. |
| 7,184,837 | B2 | 2/2007 | Goetz |
| 7,191,014 | B2 | 3/2007 | Kobayashi et al. |
| 7,209,787 | B2 | 4/2007 | Dilorenzo |

(56) References Cited

U.S. PATENT DOCUMENTS 7,211,050 B1 5/2007 Caplygin
7,216,000 B2 5/2007 Sieracki et al.
7,217,276 B2 5/2007 Henderson
7,218,968 B2 5/2007 Condie et al.
7,228,179 B2 6/2007 Campen et al.
7,231,254 B2 6/2007 DiLorenzo
7,236,830 B2 6/2007 Gliner
7,239,910 B2 7/2007 Tanner
7,239,916 B2 7/2007 Thompson et al.
7,239,926 B2 7/2007 Goetz
7,242,984 B2 7/2007 DiLorenzo
7,244,150 B1 7/2007 Brase et al.
7,252,090 B2 8/2007 Goetz
7,254,445 B2 8/2007 Law et al.
7,254,446 B1 8/2007 Erickson
7,257,447 B2 8/2007 Cates et al.
7,266,412 B2 9/2007 Stypulkowski
7,289,761 B2 10/2007 Mazar
7,294,107 B2 11/2007 Simon et al.
7,295,876 B1 11/2007 Erickson
7,299,096 B2 11/2007 Balzer et al.
7,308,302 B1 12/2007 Schuler et al.
7,313,430 B2 12/2007 Urquhart
7,324,851 B1 1/2008 DiLorenzo
7,346,282 B2 3/2008 Sakanaka et al.
7,346,382 B2 3/2008 McIntyre et al.
7,385,443 B1 6/2008 Denison
7,388,974 B2 6/2008 Yanagita
7,437,193 B2 10/2008 Parramon et al.
7,450,997 B1 11/2008 Pianca et al.
7,454,245 B2 11/2008 Armstrong et al.
7,463,928 B2 12/2008 Lee et al.
7,499,048 B2 3/2009 Sieracki et al.
7,505,815 B2 3/2009 Lee et al.
7,548,786 B2 6/2009 Lee et al.
7,565,199 B2 7/2009 Sheffield et al.
7,603,177 B2 10/2009 Sieracki et al.
7,617,002 B2 11/2009 Goetz
7,623,918 B2 11/2009 Goetz
7,650,184 B2 1/2010 Walter
7,657,319 B2 2/2010 Goetz et al.
7,672,734 B2 3/2010 Anderson et al.
7,676,273 B2 3/2010 Goetz et al.
7,680,526 B2 3/2010 McIntyre et al.
7,734,340 B2 6/2010 De Ridder
7,761,165 B1 7/2010 He et al.
7,783,359 B2 8/2010 Meadows
7,792,590 B1 9/2010 Pianca et al.
7,809,446 B2 10/2010 Meadows
7,826,902 B2 11/2010 Stone et al.
7,848,802 B2 12/2010 Goetz et al.
7,860,548 B2 12/2010 McIntyre et al.
7,896,808 B1 3/2011 Koh et al.
7,904,134 B2 3/2011 McIntyre et al.
7,945,105 B1 5/2011 Jaenisch
7,949,395 B2 5/2011 Kuzma
7,974,706 B2 7/2011 Moffitt et al.
8,000,794 B2 8/2011 Lozano
8,019,439 B2 9/2011 Kuzma et al.
8,019,443 B2 9/2011 Schleicher et al.
8,175,710 B2 5/2012 He
8,180,601 B2 5/2012 Butson et al.
8,187,209 B1 5/2012 Giuffrida
8,195,300 B2 6/2012 Gliner et al.
8,209,027 B2 6/2012 Butson et al.
8,224,450 B2 7/2012 Brase
8,257,684 B2 9/2012 Covalin et al.
8,262,714 B2 9/2012 Hulvershorn et al.
8,271,094 B1 9/2012 Moffitt et al.
8,280,514 B2 10/2012 Lozano et al.
8,295,944 B2 10/2012 Howard et al.
8,306,627 B2 11/2012 Armstrong
8,326,433 B2 12/2012 Blum et al.
8,359,107 B2 1/2013 Pianca et al.
8,364,278 B2 1/2013 Pianca et al.
8,369,954 B2 2/2013 Stack et al.
8,379,952 B2 2/2013 McIntyre et al.
8,391,985 B2 3/2013 McDonald
8,412,349 B2 4/2013 Barker
8,429,174 B2 4/2013 Ramani et al.
8,452,415 B2 5/2013 Goetz et al.
8,467,883 B2 6/2013 Chen et al.
8,473,061 B2 6/2013 Moffitt et al.
8,483,237 B2 7/2013 Zimmermann et al.
8,543,189 B2 9/2013 Paitel et al.
8,571,665 B2 10/2013 Moffitt et al.
8,589,316 B2 11/2013 Lujan et al.
8,594,800 B2 11/2013 Butson et al.
8,594,801 B2 11/2013 Corndorf et al.
8,606,360 B2 12/2013 Butson et al.
8,620,452 B2 12/2013 King et al.
8,649,845 B2 2/2014 McIntyre et al.
8,675,945 B2 3/2014 Barnhorst et al.
8,679,038 B1 3/2014 Giuffrida
8,688,235 B1 4/2014 Pianca et al.
8,744,596 B2 6/2014 Howard
8,751,008 B2 6/2014 Carlton et al.
8,751,016 B2 6/2014 Schleicher et al.
8,774,941 B2 7/2014 Pianca
8,792,993 B2 7/2014 Pianca et al.
8,831,731 B2 9/2014 Blum et al.
8,831,742 B2 9/2014 Pianca et al.
8,845,557 B1 9/2014 Giuffrida et al.
8,849,632 B2 9/2014 Sparks et al.
8,855,773 B2 10/2014 Kokones et al.
8,868,199 B2 10/2014 Kaula et al.
8,913,804 B2 12/2014 Blum et al.
8,918,183 B2 12/2014 Carlton et al.
8,918,184 B1 12/2014 Torgerson et al.
8,923,976 B2 12/2014 Johanek
8,936,622 B2 1/2015 Wales et al.
8,958,615 B2 2/2015 Blum et al.
8,972,023 B2 3/2015 Bradley et al.
8,986,382 B2 3/2015 Bentley et al.
9,020,789 B2 4/2015 Butson et al.
9,026,317 B2 5/2015 Furukawa et al.
9,039,740 B2 5/2015 Wales et al.
9,050,470 B2 6/2015 Carlton et al.
9,061,138 B2 6/2015 Pianca
9,072,905 B2 7/2015 Kokones et al.
9,081,488 B2 7/2015 Soederstroem
9,084,896 B2 7/2015 Kokones et al.
9,135,400 B2 9/2015 McIntyre et al.
9,149,630 B2 10/2015 Howard et al.
9,162,056 B2 10/2015 Pianca
9,220,889 B2 12/2015 Carlton et al.
9,227,074 B2 1/2016 Carcieri et al.
9,235,685 B2 1/2016 McIntyre et al.
9,248,272 B2 2/2016 Romero
9,248,296 B2 2/2016 Carcieri et al.
9,254,387 B2 2/2016 Blum et al.
9,272,153 B2 3/2016 Blum et al.
9,289,596 B2 3/2016 Leven
9,289,600 B2 3/2016 Govea et al.
9,302,110 B2 4/2016 Kokones et al.
9,308,372 B2 4/2016 Sparks et al.
9,310,985 B2 4/2016 Blum et al.
9,327,111 B2 5/2016 Pianca et al.
9,358,398 B2 6/2016 Moffitt et al.
9,364,665 B2 6/2016 Bokil et al.
9,381,348 B2 7/2016 Romero et al.
9,387,325 B1 7/2016 Min et al.
9,415,154 B2 8/2016 Leven
9,474,903 B2 10/2016 Chen et al.
9,492,655 B2 11/2016 Pianca et al.
9,498,620 B2 11/2016 Romero et al.
9,526,902 B2 12/2016 Blum et al.
9,533,141 B2 1/2017 Black et al.
9,566,596 B2 2/2017 Kim et al.
9,572,982 B2 2/2017 Burnes et al.
9,586,053 B2 3/2017 Moffitt et al.
9,592,389 B2 3/2017 Moffitt
9,610,435 B2 4/2017 Schleicher et al.
9,636,498 B2 5/2017 Leven

(56) References Cited

U.S. PATENT DOCUMENTS 9,649,489 B2 5/2017 Wechter et al.
9,669,210 B2 6/2017 Barker et al.
9,713,720 B2 7/2017 Zhu
9,775,988 B2 10/2017 Govea et al.
9,792,412 B2 10/2017 Moffitt et al.
9,821,167 B2 11/2017 Carcieri et al.
9,887,470 B2 2/2018 Nguyen-Stella et al.
9,925,382 B2 3/2018 Carlton et al.
9,959,940 B2 5/2018 Moffitt et al.
9,974,959 B2 5/2018 Moffitt et al.
9,987,482 B2 6/2018 Nageri et al.
10,067,659 B2 9/2018 Bokil
10,071,242 B2 9/2018 Leven
10,071,249 B2 9/2018 Zottola
10,086,205 B2 10/2018 Grill et al.
10,213,148 B2 2/2019 Min et al.
10,226,616 B2 3/2019 Barker
10,265,528 B2 4/2019 Carcieri et al.
10,265,531 B2 4/2019 Bokil
10,286,205 B2 5/2019 Steinke et al.
10,300,282 B2 5/2019 Torgerson et al.
10,335,607 B2 7/2019 Orinski
10,357,657 B2 7/2019 Moffitt et al.
10,369,364 B2 8/2019 Moffitt et al.
10,406,353 B2 9/2019 Wechter
10,485,969 B2 11/2019 Govea et al.
10,493,269 B2 12/2019 Stoffregen et al.
10,525,257 B2 1/2020 Govea et al.
10,525,266 B2 1/2020 Moffitt et al.
10,603,498 B2 3/2020 Blum et al.
10,625,072 B2 4/2020 Serrano Carmona
10,631,937 B2 4/2020 Tyulmankov et al.
10,639,488 B2 5/2020 Kalgren et al.
10,653,330 B2 5/2020 Angle et al.
10,675,468 B2 6/2020 Torgerson
10,709,886 B2 7/2020 Nagaoka et al.
10,716,505 B2 7/2020 Blum et al.
10,780,282 B2 9/2020 Mustakos et al.
10,814,127 B2 10/2020 Nageri et al.
10,814,140 B2 10/2020 Zhang et al.
10,835,739 B2 11/2020 Sandhu
10,850,101 B2 12/2020 Zhang et al.
10,857,351 B2 12/2020 Wang et al.
10,960,203 B2 3/2021 Tyler et al.
11,020,052 B2 6/2021 Zuckerman-Stark et al.
11,285,329 B2 3/2022 Carcieri et al.
11,298,550 B2 4/2022 Howard et al.
11,357,986 B2 6/2022 Steinke et al.
11,517,755 B2 12/2022 Zhang et al.
11,529,510 B2 12/2022 Leven
11,707,622 B2 7/2023 Paz et al.
11,745,010 B2 9/2023 Donega et al.
2001/0031071 A1 10/2001 Nichols et al.
2002/0032375 A1 3/2002 Bauch et al.
2002/0062143 A1 5/2002 Baudino et al.
2002/0087201 A1 7/2002 Firlik et al.
2002/0099295 A1 7/2002 Gil et al.
2002/0115603 A1 8/2002 Whitehouse
2002/0116030 A1 8/2002 Rezei
2002/0123780 A1 9/2002 Grill et al.
2002/0128694 A1 9/2002 Holsheimer
2002/0151939 A1 10/2002 Rezai
2002/0183607 A1 12/2002 Bauch et al.
2002/0183740 A1 12/2002 Edwards et al.
2002/0183817 A1 12/2002 Van Venrooij et al.
2003/0097159 A1 5/2003 Schiff et al.
2003/0149450 A1 8/2003 Mayberg
2003/0171791 A1 9/2003 KenKnight et al.
2003/0212439 A1 11/2003 Schuler et al.
2004/0034394 A1 2/2004 Woods et al.
2004/0044279 A1 3/2004 Lewin et al.
2004/0044378 A1 3/2004 Holsheimer
2004/0044379 A1 3/2004 Holsheimer
2004/0054297 A1 3/2004 Wingeier et al.
2004/0059395 A1 3/2004 North et al.
2004/0106916 A1 6/2004 Quaid et al.
2004/0133248 A1 7/2004 Frei et al.
2004/0152957 A1 8/2004 Stivoric et al.
2004/0181262 A1 9/2004 Bauhahn
2004/0186532 A1 9/2004 Tadlock
2004/0193231 A1 9/2004 David et al.
2004/0199216 A1 10/2004 Lee et al.
2004/0267330 A1 12/2004 Lee et al.
2005/0021090 A1 1/2005 Schuler et al.
2005/0033380 A1 2/2005 Tanner et al.
2005/0049649 A1 3/2005 Uders et al.
2005/0060001 A1 3/2005 Singhal et al.
2005/0060009 A1 3/2005 Goetz
2005/0070781 A1 3/2005 Dawant et al.
2005/0075689 A1 4/2005 Toy et al.
2005/0085714 A1 4/2005 Foley et al.
2005/0165294 A1 7/2005 Weiss
2005/0171587 A1 8/2005 Daglow et al.
2005/0228250 A1 10/2005 Bitter et al.
2005/0251061 A1 11/2005 Schuler et al.
2005/0261061 A1 11/2005 Nguyen et al.
2005/0261601 A1 11/2005 Schuler et al.
2005/0261747 A1 11/2005 Schuler et al.
2005/0267347 A1 12/2005 Oster
2005/0288732 A1 12/2005 Schuler et al.
2006/0004422 A1 1/2006 De Ridder
2006/0017749 A1 1/2006 McIntyre et al.
2006/0020292 A1 1/2006 Goetz et al.
2006/0069415 A1 3/2006 Cameron et al.
2006/0094951 A1 5/2006 Dean et al.
2006/0095088 A1 5/2006 De Riddler
2006/0155340 A1 7/2006 Schuler et al.
2006/0206169 A1 9/2006 Schuler
2006/0218007 A1 9/2006 Bjorner et al.
2006/0224189 A1 10/2006 Schuler et al.
2006/0235472 A1 10/2006 Goetz et al.
2006/0259079 A1 11/2006 King
2006/0259099 A1 11/2006 Goetz et al.
2007/0000372 A1 1/2007 Rezai et al.
2007/0017749 A1 1/2007 Dold et al.
2007/0027499 A1 2/2007 Maschino et al.
2007/0027514 A1 2/2007 Gerber
2007/0043268 A1 2/2007 Russell
2007/0049817 A1 3/2007 Preiss et al.
2007/0067003 A1 3/2007 Sanchez et al.
2007/0078498 A1 4/2007 Rezai et al.
2007/0083104 A1 4/2007 Butson et al.
2007/0123953 A1 5/2007 Lee et al.
2007/0129769 A1 6/2007 Bourget et al.
2007/0135855 A1 6/2007 Foshee et al.
2007/0150026 A1 6/2007 Bourget et al.
2007/0150036 A1 6/2007 Anderson
2007/0156186 A1 7/2007 Lee et al.
2007/0162086 A1 7/2007 DiLorenzo
2007/0162235 A1 7/2007 Zhan et al.
2007/0168004 A1 7/2007 Walter
2007/0168007 A1 7/2007 Kuzma et al.
2007/0179557 A1 8/2007 Maschino et al.
2007/0185544 A1 8/2007 Dawant et al.
2007/0191887 A1 8/2007 Schuler et al.
2007/0191912 A1 8/2007 Ficher et al.
2007/0197891 A1 8/2007 Shachar et al.
2007/0203450 A1 8/2007 Berry
2007/0203532 A1 8/2007 Tass et al.
2007/0203537 A1 8/2007 Goetz et al.
2007/0203538 A1 8/2007 Stone et al.
2007/0203539 A1 8/2007 Stone et al.
2007/0203540 A1 8/2007 Goetz et al.
2007/0203541 A1 8/2007 Goetz et al.
2007/0203543 A1 8/2007 Stone et al.
2007/0203544 A1 8/2007 Goetz et al.
2007/0203545 A1 8/2007 Stone et al.
2007/0203546 A1 8/2007 Stone et al.
2007/0213789 A1 9/2007 Nolan et al.
2007/0213790 A1 9/2007 Nolan et al.
2007/0244519 A1 10/2007 Keacher et al.
2007/0245318 A1 10/2007 Goetz et al.
2007/0255321 A1 11/2007 Gerber et al.
2007/0255322 A1 11/2007 Gerber et al.

(56) References Cited

U.S. PATENT DOCUMENTS

2007/0260283 A1 11/2007 Li
2007/0265664 A1 11/2007 Gerber et al.
2007/0276441 A1 11/2007 Goetz
2007/0282189 A1 12/2007 Dan et al.
2007/0288064 A1 12/2007 Butson et al.
2008/0027514 A1 1/2008 DeMulling et al.
2008/0039895 A1 2/2008 Fowler et al.
2008/0046037 A1 2/2008 Haubrich et al.
2008/0071150 A1 3/2008 Miesel et al.
2008/0081982 A1 4/2008 Simon et al.
2008/0086451 A1 4/2008 Torres et al.
2008/0091248 A1 4/2008 Libbus et al.
2008/0103533 A1 5/2008 Patel et al.
2008/0114233 A1 5/2008 McIntyre et al.
2008/0114579 A1 5/2008 McIntyre et al.
2008/0123922 A1 5/2008 Gielen et al.
2008/0123923 A1 5/2008 Gielen et al.
2008/0133141 A1 6/2008 Frost
2008/0141217 A1 6/2008 Goetz et al.
2008/0154340 A1 6/2008 Goetz et al.
2008/0154341 A1 6/2008 McIntyre et al.
2008/0163097 A1 7/2008 Goetz et al.
2008/0183256 A1 7/2008 Keacher
2008/0188734 A1 8/2008 Suryanarayanan et al.
2008/0215101 A1 9/2008 Rezai et al.
2008/0215118 A1 9/2008 Goetz et al.
2008/0227139 A1 9/2008 Deisseroth et al.
2008/0238749 A1 10/2008 Comdorf
2008/0242950 A1 10/2008 Jung et al.
2008/0261165 A1 10/2008 Steingart et al.
2008/0269588 A1 10/2008 Csavoy et al.
2008/0300654 A1 12/2008 Lambert et al.
2008/0300797 A1 12/2008 Tabibiazar et al.
2009/0016491 A1 1/2009 Li
2009/0054947 A1 2/2009 Bourn et al.
2009/0054950 A1 2/2009 Stephens
2009/0082640 A1 3/2009 Kovach et al.
2009/0082829 A1 3/2009 Panken et al.
2009/0112289 A1 4/2009 Lee et al.
2009/0118635 A1 5/2009 Lujan et al.
2009/0118786 A1 5/2009 Meadows et al.
2009/0149917 A1 6/2009 Whitehurst et al.
2009/0163975 A1 6/2009 Gerber et al.
2009/0187222 A1 7/2009 Barker
2009/0196471 A1 8/2009 Goetz et al.
2009/0196472 A1 8/2009 Goetz et al.
2009/0198306 A1 8/2009 Goetz et al.
2009/0198354 A1 8/2009 Wilson
2009/0204192 A1 8/2009 Carlton et al.
2009/0208073 A1 8/2009 McIntyre et al.
2009/0210208 A1 8/2009 McIntyre et al.
2009/0228073 A1 9/2009 Scholten
2009/0242399 A1 10/2009 Kamath et al.
2009/0270949 A1 10/2009 Kalpin et al.
2009/0276008 A1 11/2009 Lee et al.
2009/0276021 A1 11/2009 Meadows et al.
2009/0281595 A1 11/2009 King et al.
2009/0281596 A1 11/2009 King et al.
2009/0287271 A1 11/2009 Blum et al.
2009/0287272 A1 11/2009 Kokones et al.
2009/0287273 A1 11/2009 Carlton et al.
2009/0287467 A1 11/2009 Sparks et al.
2009/0299164 A1 12/2009 Singhal et al.
2009/0299165 A1 12/2009 Singhal et al.
2009/0299380 A1 12/2009 Singhal et al.
2010/0010387 A1 1/2010 Skelton et al.
2010/0010432 A1 1/2010 Skelton
2010/0010566 A1 1/2010 Thacker et al.
2010/0010646 A1 1/2010 Drew et al.
2010/0023103 A1 1/2010 Elborno
2010/0023130 A1 1/2010 Henry et al.
2010/0030312 A1 2/2010 Shen
2010/0049276 A1 2/2010 Blum et al.
2010/0049280 A1 2/2010 Goetz
2010/0057161 A1 3/2010 Machado et al.
2010/0064249 A1 3/2010 Groetken
2010/0076535 A1 3/2010 Pianca et al.
2010/0113959 A1 5/2010 Pascual-Leon et al.
2010/0121409 A1 5/2010 Kothandaraman et al.
2010/0135553 A1 6/2010 Joglekar
2010/0137944 A1 6/2010 Zhu
2010/0152604 A1 6/2010 Kuala et al.
2010/0152807 A1 6/2010 Grill et al.
2010/0179562 A1 7/2010 Linker et al.
2010/0211135 A1 8/2010 Caparso et al.
2010/0268298 A1 10/2010 Moffitt
2010/0324410 A1 12/2010 Paek et al.
2010/0331883 A1 12/2010 Schmitz et al.
2011/0004267 A1 1/2011 Meadows
2011/0005069 A1 1/2011 Pianca
2011/0040351 A1 2/2011 Buston et al.
2011/0054559 A1 3/2011 Rosenberg et al.
2011/0066407 A1 3/2011 Butson et al.
2011/0078900 A1 4/2011 Pianca et al.
2011/0093045 A1 4/2011 Moffitt
2011/0130803 A1 6/2011 McDonald
2011/0130816 A1 6/2011 Howard et al.
2011/0130817 A1 6/2011 Chen
2011/0130818 A1 6/2011 Chen
2011/0137372 A1 6/2011 Makous et al.
2011/0160796 A1 6/2011 Lane et al.
2011/0172737 A1 7/2011 Davis et al.
2011/0184487 A1 7/2011 Alberts et al.
2011/0191275 A1 8/2011 Lujan et al.
2011/0196253 A1 8/2011 McIntyre et al.
2011/0213440 A1 9/2011 Fowler et al.
2011/0224665 A1 9/2011 Crosby et al.
2011/0224680 A1 9/2011 Barker
2011/0238129 A1 9/2011 Moffitt
2011/0251583 A1 10/2011 Miyazawa et al.
2011/0270348 A1 11/2011 Goetz
2011/0306845 A1 12/2011 Osorio
2011/0306846 A1 12/2011 Osorio
2011/0307032 A1 12/2011 Goetz et al.
2011/0313485 A1 12/2011 DeMulling et al.
2011/0313500 A1 12/2011 Barker et al.
2012/0016378 A1 1/2012 Pianca et al.
2012/0027272 A1 2/2012 Akinyemi et al.
2012/0046710 A1 2/2012 Digiore et al.
2012/0046715 A1 2/2012 Moffitt et al.
2012/0071949 A1 3/2012 Pianca et al.
2012/0078106 A1 3/2012 Dentinger et al.
2012/0089205 A1 4/2012 Boyden et al.
2012/0101552 A1 4/2012 Lazarewicz et al.
2012/0116476 A1 5/2012 Kothandaraman
2012/0165898 A1 6/2012 Moffitt
2012/0165901 A1 6/2012 Zhu et al.
2012/0165911 A1 6/2012 Pianca
2012/0197375 A1 8/2012 Pianca et al.
2012/0203316 A1 8/2012 Moffitt et al.
2012/0203320 A1 8/2012 Digiore et al.
2012/0203321 A1 8/2012 Moffitt et al.
2012/0207378 A1 8/2012 Gupta et al.
2012/0226138 A1 9/2012 DeSalles et al.
2012/0229468 A1 9/2012 Lee et al.
2012/0239109 A1 9/2012 Lee
2012/0239115 A1 9/2012 Lee
2012/0265103 A1 10/2012 Policker et al.
2012/0265262 A1 10/2012 Osorio
2012/0265268 A1 10/2012 Blum et al.
2012/0271189 A1 10/2012 Nelson et al.
2012/0277833 A1 11/2012 Gerber et al.
2012/0302912 A1 11/2012 Moffitt et al.
2012/0303087 A1 11/2012 Moffitt et al.
2012/0303098 A1 11/2012 Perryman
2012/0314919 A1 12/2012 Sparks et al.
2012/0314924 A1 12/2012 Carlton et al.
2012/0316615 A1 12/2012 Digiore et al.
2012/0316619 A1 12/2012 Goetz et al.
2012/0330374 A1 12/2012 Blum et al.
2012/0330622 A1 12/2012 Butson et al.
2013/0035740 A1 2/2013 Sharma et al.
2013/0039550 A1 2/2013 Blum et al.
2013/0053926 A1 2/2013 Hincapie Ordonez et al.

(56) References Cited

U.S. PATENT DOCUMENTS

2013/0060305 A1 3/2013 Bokil
2013/0105071 A1 5/2013 Digiore et al.
2013/0116744 A1 5/2013 Blum et al.
2013/0116748 A1 5/2013 Bokil et al.
2013/0116749 A1 5/2013 Carlton et al.
2013/0116929 A1 5/2013 Carlton et al.
2013/0150922 A1 6/2013 Butson et al.
2013/0197424 A1 8/2013 Bedenbaugh
2013/0197602 A1 8/2013 Pianca et al.
2013/0226261 A1 8/2013 Sparks et al.
2013/0245722 A1 9/2013 Ternes et al.
2013/0261684 A1 10/2013 Howard
2013/0289380 A1 10/2013 Molnar et al.
2013/0289660 A1 10/2013 Molnar et al.
2013/0317572 A1 11/2013 Zhu et al.
2013/0317573 A1 11/2013 Zhu et al.
2013/0317587 A1 11/2013 Barker
2013/0325091 A1 12/2013 Pianca et al.
2014/0039586 A1 2/2014 Barker et al.
2014/0039587 A1 2/2014 Romero
2014/0063017 A1 3/2014 Kaula et al.
2014/0066999 A1 3/2014 Carcieri et al.
2014/0067018 A1 3/2014 Carcieri et al.
2014/0067022 A1 3/2014 Carcieri et al.
2014/0074180 A1 3/2014 Heldman et al.
2014/0081366 A1 3/2014 Bentley et al.
2014/0107731 A1 4/2014 Stone et al.
2014/0122379 A1 5/2014 Moffitt et al.
2014/0200633 A1 7/2014 Moffitt
2014/0243926 A1 8/2014 Carcieri
2014/0276707 A1 9/2014 Jaax
2014/0276927 A1 9/2014 Barker
2014/0277282 A1 9/2014 Jaax
2014/0277284 A1 9/2014 Chen et al.
2014/0296953 A1 10/2014 Pianca et al.
2014/0343647 A1 11/2014 Romero et al.
2014/0353001 A1 12/2014 Romero et al.
2014/0358207 A1 12/2014 Romero
2014/0358208 A1 12/2014 Howard et al.
2014/0358209 A1 12/2014 Romero et al.
2014/0358210 A1 12/2014 Howard et al.
2015/0018915 A1 1/2015 Leven
2015/0021817 A1 1/2015 Romero et al.
2015/0045864 A1 2/2015 Howard
2015/0051681 A1 2/2015 Hershey
2015/0066111 A1 3/2015 Blum et al.
2015/0066120 A1 3/2015 Govea
2015/0073431 A1 3/2015 Barker
2015/0073432 A1 3/2015 Barker
2015/0134031 A1 5/2015 Moffitt et al.
2015/0151113 A1 6/2015 Govea et al.
2015/0246231 A1 9/2015 Martens et al.
2015/0360039 A1 12/2015 Lempka et al.
2016/0001087 A1 1/2016 Moffitt
2016/0008632 A1 1/2016 Wetmore et al.
2016/0022995 A1 1/2016 Kothandaraman et al.
2016/0023008 A1 1/2016 Kothandaraman
2016/0030749 A1 2/2016 Carcieri et al.
2016/0030750 A1 2/2016 Bokil et al.
2016/0045748 A1 2/2016 Astrom et al.
2016/0082252 A1 3/2016 Hershey et al.
2016/0096025 A1 4/2016 Moffitt et al.
2016/0136429 A1 5/2016 Massoumi et al.
2016/0136443 A1 5/2016 Kothandaraman et al.
2016/0144186 A1 5/2016 Kaemmerer et al.
2016/0175594 A1 6/2016 Min et al.
2016/0206380 A1 7/2016 Sparks et al.
2016/0228692 A1 8/2016 Steinke et al.
2016/0256691 A1 9/2016 Cecchi et al.
2016/0256693 A1 9/2016 Parramon
2016/0317800 A1 11/2016 Barker
2016/0346557 A1 12/2016 Bokil
2016/0375248 A1 12/2016 Carcieri et al.
2016/0375258 A1 12/2016 Steinke
2017/0100593 A1 4/2017 Zottola
2017/0100601 A1* 4/2017 Xiao .................... A61N 1/0534
2017/0106197 A1 4/2017 Wechter et al.
2017/0197086 A1 7/2017 Howard et al.
2017/0225007 A1 8/2017 Orinski
2017/0252570 A1 9/2017 Serrano Carmona et al.
2017/0259078 A1 9/2017 Howard
2017/0304610 A1 10/2017 Huibregtse et al.
2017/0304633 A1 10/2017 Zhang
2017/0372039 A1 12/2017 Mustakos et al.
2018/0064930 A1 3/2018 Zhang et al.
2018/0078776 A1 3/2018 Mustakos et al.
2018/0104482 A1 4/2018 Bokil
2018/0104500 A1 4/2018 Blum et al.
2018/0110971 A1 4/2018 Serrano Carmona
2018/0133481 A1 5/2018 Von Zitzewitz et al.
2018/0185650 A1 7/2018 Shah
2018/0193655 A1 7/2018 Zhang et al.
2018/0214700 A1 8/2018 Vansickle et al.
2018/0264278 A1 9/2018 Laghi
2018/0272142 A1 9/2018 Zhang et al.
2018/0280698 A1 10/2018 Steinke et al.
2018/0296828 A1 10/2018 Bradley et al.
2018/0333173 A1 11/2018 Wang
2018/0369589 A1* 12/2018 Schouenborg ..... A61N 1/36132
2018/0369606 A1 12/2018 Zhang et al.
2018/0369607 A1 12/2018 Zhang et al.
2019/0015660 A1 1/2019 Zhang et al.
2019/0105503 A1 4/2019 Leven
2019/0184171 A1 6/2019 Mustakos et al.
2019/0209834 A1 7/2019 Zhang et al.
2019/0209849 A1 7/2019 Hershey et al.
2019/0262609 A1 8/2019 Brill et al.
2019/0275331 A1 9/2019 Zhu
2019/0329047 A1 10/2019 Moffitt et al.
2019/0329049 A1 10/2019 Carcieri et al.
2020/0094047 A1 3/2020 Govea et al.
2020/0139127 A1 5/2020 Zhang et al.
2020/0155854 A1 5/2020 Leven et al.
2020/0155859 A1 5/2020 Blum et al.
2020/0171298 A1 6/2020 Goetz et al.
2020/0171310 A1 6/2020 Walter et al.
2020/0179600 A1 6/2020 Zanos et al.
2020/0215330 A1 7/2020 Huertas Fernandez et al.
2020/0222704 A1 7/2020 Moffitt et al.
2020/0269053 A1 8/2020 Park
2020/0353254 A1 11/2020 OLaighin et al.
2020/0376262 A1 12/2020 Clark et al.
2020/0376263 A1 12/2020 Zhu
2020/0398057 A1 12/2020 Esteller et al.
2021/0008388 A1 1/2021 Vansickle et al.
2021/0008389 A1 1/2021 Featherstone et al.
2021/0016111 A1 1/2021 Vansickle et al.
2021/0023374 A1 1/2021 Block et al.
2021/0052893 A1 2/2021 Suri et al.
2021/0113844 A1 4/2021 Zhang et al.
2021/0128920 A1 5/2021 Grill et al.
2021/0196956 A1 7/2021 Juárez Paz
2021/0196964 A1 7/2021 Schnell et al.
2021/0205613 A1 7/2021 Bradley et al.
2021/0268268 A1 9/2021 Horn et al.
2021/0275820 A1 9/2021 Grill, Jr. et al.
2021/0387002 A1 12/2021 Bourget et al.
2022/0007980 A1 1/2022 Single
2022/0008729 A1 1/2022 Zhu
2022/0040485 A1 2/2022 Li et al.
2022/0062640 A1 3/2022 Raike et al.
2022/0072329 A1 3/2022 Howard
2022/0111213 A1 4/2022 Cassar et al.
2022/0126100 A1 4/2022 Jackson et al.
2022/0257950 A1 8/2022 Moore et al.
2022/0266026 A1 8/2022 Case et al.
2022/0296892 A1 9/2022 Esteller et al.
2022/0296893 A1 9/2022 Steinke et al.
2022/0339448 A1 10/2022 Jayakumar et al.
2022/0347479 A1 11/2022 Esteller et al.
2022/0355114 A1 11/2022 Moore et al.
2022/0355115 A1 11/2022 Moore et al.
2022/0370808 A1 11/2022 Esteller
2022/0387785 A1 12/2022 Huynh et al.

(56) References Cited

U.S. PATENT DOCUMENTS

| | | | |
|---|---|---|---|
| 2022/0395690 | A1 | 12/2022 | Haddock et al. |
| 2023/0048571 | A1 | 2/2023 | Poltorak |
| 2023/0064552 | A1 | 3/2023 | Moffitt |
| 2023/0141183 | A1 | 5/2023 | Moore et al. |
| 2023/0181089 | A1 | 6/2023 | Zhang et al. |
| 2023/0181090 | A1 | 6/2023 | Juarez Paz |
| 2023/0181906 | A1 | 6/2023 | Moore et al. |
| 2023/0248977 | A1 | 8/2023 | Esteller et al. |
| 2023/0271015 | A1 | 8/2023 | Malekmohammadi et al. |
| 2023/0277854 | A1 | 9/2023 | Gaviao Kilmar |
| 2024/0065620 | A1 | 2/2024 | Moore et al. |
| 2024/0157151 | A1 | 5/2024 | Juarez Paz |
| 2024/0198110 | A1 | 6/2024 | Moore |
| 2024/0316346 | A1 | 9/2024 | Shah et al. |
| 2024/0359015 | A1 | 10/2024 | Steinke et al. |
| 2025/0010079 | A1 | 1/2025 | Bokil |
| 2025/0050107 | A1 | 2/2025 | Moore et al. |

FOREIGN PATENT DOCUMENTS

| | | | |
|---|---|---|---|
| EP | 1166819 | | 1/2002 |
| EP | 1372780 | | 1/2004 |
| EP | 1559369 | | 8/2005 |
| WO | 97/39797 | | 10/1997 |
| WO | 98/48880 | | 11/1998 |
| WO | 01/90876 | | 11/2001 |
| WO | 02/26314 | | 4/2002 |
| WO | 02/28473 | | 4/2002 |
| WO | 02/065896 | | 8/2002 |
| WO | 02/072192 | | 9/2002 |
| WO | 03/086185 | | 10/2003 |
| WO | 2004/019799 | A2 | 3/2004 |
| WO | 2004041080 | | 5/2005 |
| WO | 2006017053 | | 2/2006 |
| WO | 2006113305 | | 10/2006 |
| WO | 20071097859 | | 8/2007 |
| WO | 20071097861 | A1 | 8/2007 |
| WO | 2007/100427 | | 9/2007 |
| WO | 2007/100428 | | 9/2007 |
| WO | 2007/112061 | | 10/2007 |
| WO | 2009097224 | | 8/2009 |
| WO | 2010/109448 | | 9/2010 |
| WO | 2010/120823 | A2 | 10/2010 |
| WO | 2011025865 | | 3/2011 |
| WO | 2011/139779 | A1 | 11/2011 |
| WO | 2011/159688 | A2 | 12/2011 |
| WO | 2012088482 | | 6/2012 |
| WO | 2016/025913 | | 2/2016 |
| WO | 2016081099 | | 5/2016 |
| WO | 2016112398 | | 7/2016 |

OTHER PUBLICATIONS

Butson et al., "Sources and Effects of Electrode Impedance During Deep Brain Stimulation", Clinical Neurophysiology, 117:44 7-454, Dec. 2005.

D'Haese et al., "Computer-Aided Placement of Deep Brain Stimulators: From Planning to Intraoperative Guidance", IEEE Transaction on Medical Imaging, 24:1469-1478, Nov. 2005.

Gross et al., "Electrophysiological Mapping for the Implantation of Deep Brain Stimulators for Parkinson's Disease and Tremor", Movement Disorders, 21 :S259-S283, Jun. 2006.

Halpern et al., "Brain Shift During Deep Brain Stimulation Surgery for Parkinson's Disease", Stereotact Funct. Neurosurg., 86:37-43, published online Sep. 2007.

Herzog et al., "Most Effective Stimulation Site in Subthalamic Deep Brain Stimulation for Parkinson's Disease", Movement Disorders, 19:1050-1099, published on line Mar. 2004.

Jeon et al., A Feasibility Study of Optical Coherence Tomography for Guiding Deep Brain Probes, Journal of Neuroscience Methods, 154:96-101, Jun. 2006.

Khan et al., "Assessment of Brain Shift Related to Deep Brain Stimulation Surgery", Sterreotact Funct. Neurosurg., 86:44-53, published online Sep. 2007.

Koop et al., "Improvement in a Quantitative Measure of Bradykinesia After Microelectrode Recording in Patients with Parkinson's Disease During Deep Brain Stimulation Surgery", Movement Disorders, 21 :673-678, published on line Jan. 2006.

Lemaire et al., "Brain Mapping in Stereotactic Surgery: A Brief Overview from the Probabilistic Targeting to the Patient-Based Anatomic Mapping", NeuroImage, 37:S109-S115, available online Jun. 2007.

Machado et al., "Deep Brain Stimulation for Parkinson's Disease: Surgical Technique and Perioperative Management", Movement Disorders, 21 :S247-S258, Jun. 2006.

Maks et al., "Deep Brain Stimulation Activation Volumes and Their Association with Neurophysiological Mapping and Therapeutic Outcomes", Downloaded from jnnp.bmj.com, pp. 1-21, published online Apr. 2008.

Moran et al., "Real-Time Refinment of Subthalamic Nucleous Targeting Using Bayesian Decision-Making on the Root Mean Square Measure", Movement Disorders, 21: 1425-1431, published online Jun. 2006.

Sakamoto et al., "Homogeneous Fluorescence Assays for RNA Diagnosis by Pyrene-Conjugated 2'-0-Methyloligoribonucleotides", Nucleosides, Nucleotides, and Nucleric Acids, 26:1659-1664, on line publication Oct. 2007.

Winkler et al., The First Evaluation of Brain Shift During Functional Neurosurgery by Deformation Field Analysis, J. Neural. Neurosurg. Psychiatry, 76:1161-1163, Aug. 2005.

Yelnik et al., "A Three-Dimensional, Histological and Deformable Atlas of the Human Basal J Ganglia. I. Atlas Construction Based on Immunohistochemical and MRI Data", NeuroImage, 34:618,-638,Jan. 2007.

Ward, H. E., et al., "Update on deep brain stimulation for neuropsychiatric disorders," Neurobiol Dis 38 (3) (2010), pp. 346-353.

Alberts et al. "Bilateral subthalamic stimulation impairs cognitive-motor performance in Parkinson's disease patients." Brain (2008), 131, 3348-3360, Abstract.

Grill, WM., et al., "Electrical properties of implant encapsulation tissue", Ann Biomed Eng. vol. 22. (1994),23-33.

An, et al., "Prefrontal cortical projections to longitudinal columns in the midbrain periaqueductal gray in macaque monkeys," J Comp Neural 401 (4) (1998), pp. 455-479.

Haslinger, B., et al., "Frequency-correlated decreases of motor cortex activity associated with subthalamic nucleus stimulation in Parkinson's disease.", Neuroimage 28(3). (Nov. 15, 2005),598-606.

Carmichael, S. T., et al., "Connectional networks within the orbital and medial prefrontal cortex of macaque monkeys," J Comp Neural 371 (2) (1996), pp. 179-207.

Croxson, et al., "Quantitative investigation of connections of the prefrontal cortex in the human and macaque using probabilistic diffusion tractography," J Neurosci 25 (39) (2005), pp. 8854-8866.

Frankemolle, et al., "Reversing cognitive-motor impairments in Parkinson's disease patients using a computational modelling approach to deep brain stimulation programming," Brain 133 (2010), pp. 746-761.

Freedman, et al., "Subcortical projections of area 25 (subgenual cortex) of the macaque monkey," J Comp Neurol 421 (2) (2000), pp. 172-188.

Giacobbe, et al., "Treatment resistant depression as a failure of brain homeostatic mechanisms: implications for deep brain stimulation," Exp Neural 219 (1) (2009), pp. 44-52.

Goodman, et al., "Deep brain stimulation for intractable obsessive compulsive disorder: pilot study using a blinded, staggered-onset design," Biol Psychiatry 67 (6) (2010), pp. 535-542.

Greenberg, et al., "Deep brain stimulation of the ventral internal capsule/ventral striatum for obsessive-compulsive disorder: worldwide experience," Mol Psychiatry 15 (1) (2010), pp. 64-79.

Greenberg et al., "Three-year outcomes in deep brain stimulation for highly resistant obsessive-compulsive disorder," Neuropsychopharmacology 31 (11) (2006), pp. 2384-2393.

(56) References Cited

OTHER PUBLICATIONS

Gutman, et al., "A tractography analysis of two deep brain stimulation white matter targets for depression," Biol Psychiatry 65 (4) (2009), pp. 276-282.
Haber, et al., "Reward-related cortical inputs define a large striatal region in primates that interface with associative cortical connections, providing a substrate for incentive-based learning," J Neurosci 26 (32) (2006), pp. 8368-8376.
Haber, et al., "Cognitive and limbic circuits that are affected by deep brain stimulation," Front Biosci 14 (2009), pp. 1823-1834.
Hines, M. L., et al., "The Neuron simulation environment," Neural Comput., 9(6) (Aug. 15, 1997), pp. 1179-1209.
Hua, et al., "Tract probability maps in stereotaxic spaces: analyses of white matter anatomy and tract-specific quantification," Neuroimage 39 (1) (2008), pp. 336-347.
Johansen-Berg, et al., "Anatomical connectivity of the subgenual cingulate region targeted with deep brain stimulation for treatment-resistant depression," Cereb Cortex 18 (6) (2008), pp. 1374-1383.
Kopell, et al., "Deep brain stimulation for psychiatric disorders," J Clin Neurophysiol 21 (1) (2004), pp. 51-67.
Lozano, et al., "Subcallosal cingulate gyrus deep brain stimulation for treatment-resistant depression," Biol Psychiatry 64 (6) (2008), pp. 461-467.
Lujan, et al., "Tracking the mechanisms of deep brain stimulation for neuropsychiatric disorders," Front Biosci 13 (2008), pp. 5892-5904.
Lujan, J.L. et al., "Automated 3-Dimensional Brain Atlas Fitting to Microelectrode Recordings from Deep Brain Stimulation Surgeries," Stereotact. Fune!. Neurosurg. 87(2009), pp. 229-240.
Machado. et al., "Functional topography of the ventral striatum and anterior limb of the internal capsule determined by electrical stimulation of awake patients," Clin Neurophysiol 120 (11) (2009), pp. 1941-1948.
Malone, et al., "Deep brain stimulation of the ventral capsule/ventral striatum for treatment-resistant depression," Biol Psychiatry 65 (4) (2009), pp. 267-275.
Mayberg, H. S., et al., "Deep brain stimulation for treatment-resistant depression," Neuron, 45(5) (Mar. 3, 2005), pp. 651-660.
Mayberg, H. S., et al., "Limbic-cortical dysregulation: a proposed model of depression," J Neuropsychiatry Clin Neurosci. 9 (3) (1997), pp. 471-481.
McIntyre,C. C., et al., "Network perspectives on the mechanisms of deep brain stimulation," Neurobiol Dis 38 (3) (2010), pp. 329-337.
Miocinovic, S., et al., "Experimental and theoretical characterization of the voltage distribution generated by deep brain stimulation," Exp Neurol 216 (i) (2009), pp. 166-176.
Nuttin, et al., "Electrical stimulation in anterior limbs of internal capsules in patients with obsessive-compulsive disorder," Lancet 354 (9189) (1999), p. 1526.
Saxena, et al., "Cerebral glucose metabolism in obsessive-compulsive hoarding," Am J Psychiatry. 161 (6) (2004), pp. 1038-1048.
Viola, et al., "Importance-driven focus of attention," IEEE Trans Vis Comput Graph 12 (5) (2006), pp. 933-940.
Wakana, S., et al., "Reproducibility of quantitative tractography methods applied to cerebral white matter," Neuroimage 36 (3) (2007), pp. 630-644.
Mayr et al., "Basic Design and Construction of the Vienna FES Implants: Existing Solutions and Prospects for New Generations of Implants", Medical Engineering & Physics, 2001; 23:53-60.
Nowinski, W. L., et al., "Statistical analysis of 168 bilateral subthalamic nucleus implantations by means of the probabilistic functional atlas.", Neurosurgery 57(4 Suppl) (Oct., 2005),319-30.
Obeso, J. A., et al., "Deep-brain stimulation of the subthalamic nucleus or the pars interna of the globus pallidus in Parkinson's disease.", N Engl J Med., 345{131. The Deep-Brain Stimulation for Parkinson's Disease Study Group, (Sep. 27, 2001 ),956-63.
Butson et al.. "Current Steering to control the volume of tissue activated during deep brain stimulation," vol. 1, No. 1, Dec. 3, 2007, pp. 7-15.
Patrick, S. K., et al., "Quantification of the UPDRS rigidity scale", IEEE Transactions on Neural Systems and Rehabilitation Engineering, [see also IEEE Trans. on Rehabilitation Engineering 9(1). (2001),31-41.
Phillips, M. D., et al., "Parkinson disease: pattern of functional MR imaging activation during deep brain stimulation of subthalamic nucleus—initial experience", Radiology 239(1). (Apr. 2006),209-16.
Ericsson, A. et al., "Construction of a patient-specific atlas of the brain: Application to normal aging," Biomedical Imaging: From Nano to Macro, ISBI 2008, 5th IEEE International Symposium, May 14, 2008, pp. 480-483.
Kaikai Shen et al., "Atlas selection strategy using least angle regression in multi-atlas segmentation propagation," Biomedical Imaging: From Nano to Macro, 2011, 8th IEEE International Symposium, ISBI 2011, Mar. 30, 2011, pp. 1746-1749.
Liliane Ramus et al., "Assessing selection methods in the cotnext of multi-atlas based segmentation," Biomedical Imaging: From Nano to Macro, 2010, IEEE International Symposium, Apr. 14, 2010, pp. 1321-1324.
Olivier Commowick et al., "Using Frankenstein's Creature Paradigm to Build a Patient Specific Atlas," Sep. 20, 2009, Medical Image Computing and Computer-Assisted Intervention, pp. 993-1000.
Lotjonen J.M.P. et al., "Fast and robust multi-atlas segmentation of brain magnetic resonance images," NeuroImage, Academic Press, vol. 49, No. 3, Feb. 1, 2010, pp. 2352-2365.
Mcintyre, C. C., et al., "How does deep brain stimulation work? Present understanding and future questions.", J Clin Neurophysiol. 21 (1 ). (Jan.-Feb. 2004 ),40-50.
Sanchez Castro et al., "A cross validation study of deep brain stimulation targeting: From experts to Atlas-Based, Segmentation-Based and Automatic Registration Algorithms," IEEE Transactions on Medical Imaging, vol. 25, No. 11, Nov. 1, 2006, pp. 1440-1450.
Plaha, P. , et al., "Stimulation of the caudal zona incerta is superior to stimulation of the subthalamic nucleus in improving contralateral parkinsonism.", Brain 129{Pt 7) (Jul. 2006), 1732-4 7.
Rattay, F, "Analysis of models for external stimulation of axons", IEEE Trans. Biomed. Eng. vol. 33 (1986),974-977.
Rattay, F., "Analysis of the electrical excitation of CNS neurons", IEEE Transactions on Biomedical Engineering 45 (6). (Jun. 1998),766-772.
Rose, T. L., et al., "Electrical stimulation with Pt electrodes. VIII. Electrochemically safe charge injection limits with 0.2 ms pulses [neuronal application]", IEEE Transactions on Biomedical Engineering, 37(11 }, (Nov. 1990), 1118-1120.
Rubinstein, J. T., et al., "Signal coding in cochlear implants: exploiting stochastic effects of electrical stimulation", Ann Otol Rhinol Laryngol Suppl.. 191, (Sep. 2003), 14-9.
Schwan, H.P., et al., "The conductivity of living tissues.", Ann NY Acad Sci., 65(6). (AUQ., 1957), 1007-13.
Taylor, R. S., et al., "Spinal cord stimulation for chronic back and leg pain and failed back surgery syndrome: a systematic review and analysis of prognostic factors", Spine 30(1 ). (Jan. 1, 2005), 152-60.
Siegel, Ralph M. et al., "Spatiotemporal dynamics of the functional architecture for gain fields in inferior parietal lobule of behaving monkey," Cerebral Cortex, New York, NY, vol. 17, No. 2, Feb. 2007, pp. 378-390.
Klein, A. et al., "Evaluation of 14 nonlinear deformation algorithms applied to human brain MRI registration," NeuroImage, Academic Press, Orlando, FL, vol. 46, No. 3, Jul. 2009, pp. 786-802.
Geddes, L. A., et al., "The specific resistance of biological material—a compendium of data for the biomedical engineer and physiologist.", Med Biol Ena. 5(3). (May 1967),271-93.
Gimsa, J., et al., "Choosing electrodes for deep brain stimulation experiments—electrochemical considerations.", J Neurosci Methods, 142(2), (Mar. 30, 2005),251-65.
Vidailhet, M. , et al., "Bilateral deep-brain stimulation of the globus pallidus in primary generalized dystonia", N Engl J Med. 352(5) (Feb. 3, 2005),459-67.

(56) References Cited

OTHER PUBLICATIONS

Izad, Oliver, "Computationally Efficient Method in Predicating Axonal Excitation," Dissertation for Master Degree, Department of Biomedical Engineering, Case Western Reserve University, May 2009.
Dice, Lee R., "Measures of the Amount of Ecologic Association Between Species," Ecology 26(3) (1945): 297-302. doi: 10.2307/1932409, http://jstor.org/stable/1932409.
Rand, WM., "Objective criteria for the evaluation of clustering methods," Journal of the American Statistical Association (American Statistical Association) 66 (336) (1971 ): 846-850, doi:10.2307/2284239, http://jstor.org/stable/2284239.
Hubert, Lawrence et al., "Comparing partitions," Journal of Classification 2(1) (1985): 193-218, doi:10.1007/BF01908075.
Cover, T.M. et al., "Elements of information theory," (1991) John Wiley & Sons, New York, NY.
Meila, Marina, "Comparing Clusterings by the Variation of Information," Learning Theory and Kernel Machines (2003): 173-187.
Viola, P., et al., "Alignment by maximization of mutual information", International Journal of Com outer Vision 24(2). ( 1997), 137-154.
Butson et al. "StimExplorer: Deep Brain Stimulation Parameter Selection Software System," Acta Neurochirugica, Jan. 1, 2007, vol. 97, No. 2, pp. 569-574.
Butson et al. "Role of Electrode Design on the Volume of Tissue Activated During Deep Brain Stimulation," Journal of Neural Engineering, Mar. 1, 2006, vol. 3, No. 1, pp. 1-8.
Volkmann et al., Indroduction to the Programming of Deep Brain Stimulators, Movement Disorders, vol. 17, Suppl. 3, pp. S181-S187 (2002).
Miocinovic et al. "Cicerone: Stereotactic Neurophysiological Recording and Deep Brain Stimulation Electrode Placement Software System," Acta Neurochirurgica Suppl., Jan. 1, 2007, vol. 97, No. 2, pp. 561-567.
Schmidt et al. "Sketching and Composing Widgets for 3D Manipulation," Eurographics, Apr. 2008, vol. 27, No. 2, pp. 301-310.
Volkmann, J. , et al., "Basic algorithms for the programming of deep brain stimulation in Parkinson's disease", Mov Disord., 21 Suppl 14. (Jun. 2006),S284-9.
Walter, B. L., et al., "Surgical treatment for Parkinson's disease", Lancet Neural. 3(12). (Dec. 2004),719-28.
Wei, X. F., et al., "Current density distributions, field distributions and impedance analysis of segmented deep brain stimulation electrodes", J Neural Eng.. 2(4). (Dec. 2005), 139-47.
Zonenshayn, M. , et al., "Location of the active contact within the subthalamic nucleus (STN) in the treatment of idiopathic Parkinson's disease.", Surg Neurol., 62(3) (Sep. 2004),216-25.
Da Silva et al (A primer on diffusion tensor imaging of anatomical substructures. Neurosurg Focus 15(1): p. 1-4, Article 4, 2003.).
Micheli-Tzanakou, E., et al., "Computational Intelligence for target assesment in Parkinson's disease", Proceedings of SPIE vol. 4479. Applications and Science of Neural Networks, Fuzzy Systems, and Evolutionary Computation IV,(2001),54-69.
Grill, W. M., "Stimulus waveforms for selective neural stimulation", IEEE Engineering in Medicine and Biology Magazine, 14(4}, (Jul.-Aug. 1995), 375-385.
Miocinovic, S., et al., "Sensitivity of temporal excitation properties to the neuronal element activated by extracellular stimulation", J Neurosci Methods. 132(1). (Jan. 15, 2004), 91-9.
Hunka, K. et al., Nursing Time to Program and Assess Deep Brain Stimulators in Movement Disorder Patients, J. Neursci Nurs., 37: 204-10 (Aug. 2005).
Moss, J. , et al., "Electron microscopy of tissue adherent to explanted electrodes in dystonia and Parkinson's disease", Brain, 127{Pt 12). (Dec. 2004 ),2755-63.
Montgomery, E. B., et al., "Mechanisms of deep brain stimulation and future technical developments.", Neurol Res. 22(3). (Apr. 2000),259-66.
Merrill, D. R., et al., "Electrical stimulation of excitable tissue: design of efficacious and safe protocols", J Neurosci Methods. 141(2), (Feb. 15, 2005), 171-98.
Fisekovic et al., "New Controller for Functional Electrical Stimulation Systems", Med. Eng. Phys. 2001; 23:391-399.
International Search Report and Written Opinion for PCT Application No. PCT/US2023/013122 mailed Jun. 5, 2023.
Alo, K. M., et al., "New trends in neuromodulation for the management of neuropathic pain," Neurosurgery, 50(4), (Apr. 2002), pp. 690-703, discussion pp. 703-704.
Ashby, P., et al., "Neurophysiological effects of stimulation through electrodes in the human subthalamic nucleus," Brain, 122 (PI 10), (Oct. 1999), pp. 1919-1931.
Baker, K. B., et al., "Subthalamic nucleus deep brain stimulus evoked potentials: Physiological and therapeutic implications," Movement Disorders, 17(5), (Sep./Ocl. 2002), pp. 969-983.
Bammer, R, et al., "Diffusion tensor imaging using single-shot Sense-EPI", Magn Reson Med., 48(1 ), (Jul. 2002), pp. 128-136.
Basser, P J., et al., "MR diffusion tensor spectroscopy and imaging," Biophys J., 66(1 ), (Jan. 1994), pp. 259-267.
Basser, P J., et al., "New currents in electrical stimulation of excitable tissues," Annu Rev Biomed Eng., 2, (2000), pp. 377-397.
Benabid, AL., et al., "Chronic electrical stimulation of the ventralis intermedius nucleus of the thalamus as a treatment of movement disorders," J. Neurosurg., 84(2), (Feb. 1996), pp. 203-214.
Benabid, AL., et al., "Combined (Ihalamotoy and stimulation) stereotactic surgery of the VIM thalamic nucleus for bilateral Parkinson disease," Appl Neurophysiol, vol. 50, (1987), pp. 344-346.
Benabid, A L., et al., "Long-term suppression of tremor by chronic stimulation of the ventral intermediate thalamic nucleus," Lancet, 337 (8738), (Feb. 16, 1991 ), pp. 403-406.
Benoit M. Dawant et al: "The VU-DBS project: integrated and computer-assisted planning, intra-operative placement, and post-operative programming of deep-brain stimulators", Proceedings of SPIE, vol. 6509, Mar. 6, 2007 (Mar. 6, 2007), 11 pages.
Christensen, Gary E., et al., "Volumetric transformation of brain anatomy," IEEE Transactions on Medical Imaging, 16 (6), (Dec. 1997), pp. 864-877.
Cooper, S , et al., "Differential effects of thalamic stimulation parameters on tremor and paresthesias in essential tremor," Movement Disorders, 17(Supp. 5), (2002), p. S193.
Coubes, P, et al., "Treatment of DYT1-generalised dystonia by stimulation of the internal globus pallidus," Lancet, 355 (9222), (Jun. 24, 2000), pp. 2220-2221.
Pulliam CL, Heldman DA, Orcutt TH, Mera TO, Giuffrida JP, Vitek JL. Motion sensor strategies for automated optimization of deep brain stimulation in Parkinson's disease. Parkinsonism Relat Disord. Apr. 2015; 21(4):378-82.
Dawant, B. M., et al., "Compuerized atlas-guided positioning of deep brain stimulators: a feasibility study," Biomedical Image registration, Second International Workshop, WBIR 2003, Revised Papers (Lecture notes in Comput. Sci. vol. (2717), Springer-Verlag Berlin, Germany(2003), pp. 142-150.
Finnis, K. W., et al., "3-D functional atalas of subcortical structures for image guided stereotactic neurosurgery," Neuroimage, vol. 9, No. 6, Iss. 2 (1999), p. S206.
Finnis, K. W., et al., "3D Functional Database of Subcorticol Structures for Surgical Guidance in Image Guided Stereotactic Neurosurgery," Medical Image Computing and Computer-Assisted Intervention—MICCAI'99, Second International Conference. Cambridge, UK, Sep. 19-22, 1999, Proceedings (1999), pp. 758-767.
Finnis, K. W., et al., "A 3-Dimensional Database of Deep Brain Functional Anatomy, and Its Application to Image-Guided Neurosurgery," Proceedings of the Third International Conference on Medical Image Computing and Computer-Assisted Intervention. Lecture Notes In Computer Science; vol. 1935 (2000), pp. 1-8.
Finnis, K. W., et al., "A functional database for guidance of surgical and therapeutic procedures in the deep brain," Proceedings of the 22nd Annual International Conference of the IEEE Engineering in Medicine and Biology Society, vol. 3 (2000), pp. 1787-1789.

(56) References Cited

OTHER PUBLICATIONS

Finnis, K. W., et al., "Application of a Population Based Electrophysiological Database to the Planning and Guidance of Deep Brain Stereotactic Neurosurgery," Proceedings of the 5th International Conference on Medical Image Computing and Computer-Assisted Intervention—Part 11, Lecture Notes In Computer Science; vol. 2489 (2002), pp. 69-76.
Finnis, K. W., et al., "Subcortical physiology deformed into a patient-specific brain atlas for image-guided stereotaxy," Proceedings of SPIE—vol. 4681 Medical Imaging 2002: Visualization, Image-Guided Procedures, and Display (May 2002), pp. 184-195.
Finnis, Krik W., et al., "Three-Dimensional Database of Subcortical Electrophysiology for Image-Guided Stereotatic Functional Neurosurgery," IEEE Transactions on Medical Imaging, 22(1) (Jan. 2003), pp. 93-104.
Gabriels, L , et al., "Deep brain stimulation for treatment-refractory obsessive-compulsive disorder: psychopathological and neuropsychological outcome in three cases," Acta Psychiatr Scand., 107(4) (2003), pp. 275-282.
Gabriels, LA., et al., "Long-term electrical capsular stimulation in patients with obsessive-compulsive disorder," Neurosurgery, 52(6) (Jun. 2003), pp. 1263-1276.
Goodall, E. V., et al., "Modeling study of activation and propagation delays during stimulation of peripheral nerve fibers with a tripolar cuff electrode," IEEE Transactions on Rehabilitation Engineering, [see also IEEE Trans. on Neural Systems and Rehabilitation], 3(3) (Sep. 1995), pp. 272-282.
Goodall, E. V., et al., "Position-selective activation of peripheral nerve fibers with a cuff electrode," IEEE Transactions on Biomedical Engineering, 43(8) (Aug. 1996), pp. 851-856.
Goodall, E. V., "Simulation of activation and propagation delay during tripolar neural stimulation," Proceedings of the 15th Annual International Conference of the IEEE Engineering in Medicine and Biology Society (1993), pp. 1203-1204.
Grill, WM., "Modeling the effects of electric fields on nerve fibers: influence of tissue electrical properties," IEEE Transactions on Biomedical Engineering, 46(8) (1999), pp. 918-928.
Grill, W. M., et al., "Neural and connective tissue response to long-term implantation of multiple contact nerve cuff electrodes," J Biomed Mater Res., 50(2) (May 2000), pp. 215-226.
Grill, W. M., "Neural modeling in neuromuscular and rehabilitation research," Proceedings of the 23rd Annual International Conference of the IEEE Engineering in Medicine and Biology Society, vol. 4 (2001 ), pp. 4065-4068.
Grill, W. M., et al., "Non-invasive measurement of the input-output properties of peripheral nerve stimulating electrodes," Journal of Neuroscience Methods, 65(1) (Mar. 1996), pp. 43-50.
Grill, W. M., et al., "Quantification of recruitment properties of multiple contact cuff electrodes," IEEE Transactions on Rehabilitation Engineering, [see also IEEE Trans. on Neural Systems and Rehabilitation], 4(2) (Jun. 1996), pp. 49-62.
Grill, W. M., "Spatially selective activation of peripheral nerve for neuroprosthetic applications," Ph.D. Case Western Reserve University, (1995), pp. 245 pages.
Grill, W. M., "Stability of the input-output properties of chronically implanted multiple contact nerve cuff stimulating electrodes," IEEE Transactions on Rehabilitation Engineering [see also IEEE Trans. on Neural Systems and Rehabilitation] (1998), pp. 364-373.
Grill, W. M., et al., "Deep brain stimulation creates an informational lesion of the stimulated nucleus", Neuroreport. 15I7t (May 19, 2004 ), 1137-40.
Grill, W. M., et al., "Temporal stability of nerve cuff electrode recruitment properties," IEEE 17th Annual Conference Engineering in Medicine and Biology Society, vol. 2 (1995), pp. 1089-1090.
Gross, RE., et al., "Advances in neurostimulation for movement disorders," Neurol Res., 22(3) (Apr. 2000), pp. 247-258.
Guridi et al., "The subthalamic nucleus, hemiballismus and Parkinson's disease: reappraisal of a neurological dogma," Brain, vol. 124, 2001, pp. 5-19.
Haberler, C, et al., "No tissue damage by chronic deep brain stimulation in Parkinson's disease," Ann Neurol., 48(3) (Sep. 2000), pp. 372-376.
Hamel, W, et al., "Deep brain stimulation of the subthalamic nucleus in Parkinson's disease: evaluation of active electrode contacts," J Neurol Neurosurg Psychiatry, 74(8) (Aug. 2003), pp. 1036-1046.
Hanekom, "Modelling encapsulation tissue around cochlear implant electrodes," Med. Biol. Eng. Comput. vol. 43 (2005), pp. 47-55.
Haueisen, J , et al., "The influence of brain tissue anisotropy on human EEG and MEG," Neuroimage, 15(1) (Jan. 2002), pp. 159-166.
D'Haese et al. Medical Image Computing and Computer-Assisted Intervention—MICCAI 2005 Lecture Notes in Computer Science, 2005, vol. 3750, 2005, 427-434.
Rohde et al. IEEE Transactions on Medical Imaging, vol. 22 No. 11, 2003 p. 1470-1479.
Dawant et al., Biomedical Image Registration. Lecture Notes in Computer Science, 2003, vol. 2717, 2003, 142-150.
Miocinovic et al., "Stereotactiv Neurosurgical Planning, Recording, and Visualization for Deep Brain Stimulation in Non-Human Primates", Journal of Neuroscience Methods, 162:32-41, Apr. 5, 2007, XP022021469.
Gemmar et al., "Advanced Methods for Target Navigation Using Microelectrode Recordings in Stereotactic Neurosurgery for Deep Brain Stimulation", 21st IEEE International Symposium on Computer-Based Medical Systems, Jun. 17, 2008, pp. 99-104, XP031284774.
Acar et al., "Safety Anterior Commissure-Posterior Commissure-Based Target Calculation of the Subthalamic Nucleus in Functional Stereotactic Procedures", Stereotactic Funct. Neurosura., 85:287-291, Aug. 2007.
Andrade-Souza, "Comparison of Three Methods of Targeting the Subthalamic Nucleus for Chronic Stimulation in Parkinson's Disease", Neurosurgery, 56:360-368, Apr. 2005.
Anheim et al., "Improvement in Parkinson Disease by Subthalamic Nucleus Stimulation Based on Electrode Placement", Arch Neural., 65:612-616, May 2008.
Mitra PP, Pesaran B. Analysis of dynamic brain imaging data. Biophys J. Feb. 1999;76(2):691-708. doi: 10.1016/S0006-3495(99)77236-X. PMID: 9929474; PMCID: PMC1300074.
Hammer N, Glätzner J, Feja C, Kühne C, Meixensberger J, et al. (2015) Human Vagus Nerve Branching in the Cervical Region. Plos One 10(2): e0118006. Published: Feb. 13, 2015. https://doi.org/10.1371/journal.pone.0118006.
Mcintyre, Cameron , et al., "Finite element analysis of the current-density and electric field generated by metal microelectrodes", Ann Biomed Eng . 29(3), (2001 ),227-235.
Foster, K. R., et al., "Dielectric properties of tissues and biological materials: a critical review.", Grit Rev Biomed Ena. 17(1 ). {1989),25-104.
Limousin, P., et al., "Electrical stimulation of the subthalamic nucleus in advanced Parkinson's disease", N Engl J Med .. 339(16), (Oct. 15, 1998), 1105-11.
Kitagawa, M., et al., "Two-year follow-up of chronic stimulation of the posterior subthalamic white matter for tremor-dominant Parkinson's disease.", Neurosurgery. 56(2). (Feb. 2005),281-9.
Johnson, M. D., et al., "Repeated voltage biasing improves unit recordings by reducing resistive tissue impedances", IEEE Transactions on Neural Systems and Rehabilitation Engineering, [see also IEEE Trans. on Rehabilitation Engineering (2005), 160-165.
Holsheimer, J. , et al., "Chronaxie calculated from current-duration and voltage-duration data", J Neurosci Methods. 97(1). (Apr. 1, 2000),45-50.
Hardman, C. D., et al., "Comparison of the basal ganglia in rats, marmosets, macaques, baboons, and humans: volume and neuronal number for the output, internal relay, and striatal modulating nuclei", J Comp Neurol., 445(3). (Apr. 8, 2002),238-55.
Hashimoto, T. , et al., "Stimulation of the subthalamic nucleus changes the firing pattern of pallidal neurons", J Neurosci. 23(5). (Mar. 1, 2003), 1916-23.
Hershey, T., et al., "Cortical and subcortical blood flow effects of subthalamic nucleus stimulation in PD.", Neurology 61(6). (Sep. 23, 2003),816-21.

(56) References Cited

OTHER PUBLICATIONS

Hemm, S. , et al., "Evolution of Brain Impedance in Dystonic Patients Treated by GPi Electrical Stimulation", Neuromodulation 7(2) (Apr. 2004),67-75.
Hemm, S., et al., "Deep brain stimulation in movement disorders: stereotactic coregistration of two-dimensional electrical field modeling and magnetic resonance imaging.", J Neurosurg. 103(6): (Dec. 2005),949-55.
C.R. Butson, J. Hall, J. Henderson, C. McIntyre. Patient-Specific Models of Deep Brain Stimulation: 3D Visualization of Anatomy, Electrode and Volume of Activation as a Function of Stimulation Parameters Program No. 1011.11. 2004 Abstract. Washington, DC: Society for Neuroscience, 2004. Online.
Trost M, Su S, Su P, Yen RF, Tseng HM, Barnes A, Ma Y, Eidelberg D. Network modulation by the subthalamic nucleus in the treatment of Parkinson's disease. Neuroimage. May 15, 2006;31(1):301-7. doi: 10.1016/j.neuroimage.2005.12.024. Epub Feb. 8, 2006.
Mcintyre, Cameron C., et al., "Electric Field and Stimulating Influence generated by Deep Brain Stimulation of the Subthalamaic Nucleus," Clinical Neurophysiology, 115(3) (Mar. 2004), pp. 589-595.
Mcintyre, Cameron C., et al., "Electric field generated by deep brain stimulation of the subthalamic nucleus," Biomedical Engineering Society Annual Meeting, Nashville TN (Oct. 2003), 16 pages.
Mcintyre, Cameron C., et al., "Excitation of central nervous system neurons by nonuniform electric fields," Biophys. J., 76(2) (1999), pp. 878-888.
McNeal, DR., et al., "Analysis of a model for excitation of myelinated nerve," IEEE Trans Biomed Eng., vol. 23 (1976), pp. 329-337.
McNaughtan et al., "Electrochemical Issues in Impedance Tomography", 1st World Congress on Industrial Process Tomography, Buxton, Greater Manchester, Apr. 14-17, 1999.
Miocinovic, S., et al., "Computational analysis of subthalamic nucleus and lenticular fasciculus activation during therapeutic deep brain stimulation," J Neurophysiol., 96(3) (Sep. 2006), pp. 1569-1580.
Miranda, P. C., et al., "The distribution of currents inducedin the brain by Magnetic Stimulation: a finite element analysis incorporating OT-MRI-derived conductivity data," Proc. Intl. Soc. Mag. Reson. Med. 9 (2001 ), p. 1540.
Miranda, P. C., et al., "The Electric Field Induced in the Brain by Magnetic Stimulation: A 3-D Finite-Element Analysis of the Effect of Tissue Heterogeneity and Anisotropy," IEEE Transactions on Biomedical Engineering, 50(9) (Sep. 2003), pp. 1074-1085.
Moffitt, MA., et al., "Prediction of myelinated nerve fiber stimulation thresholds: limitations of linear models," IEEE Transactions on Biomedical Engineering, 51 (2) (2003), pp. 229-236.
Moro, E, et al., "The impact on Parkinson's disease of electrical parameter settings in STN stimulation," Neurology, 59 (5) (Sep. 10, 2002), pp. 706-713.
Nowak, LG., et al., "Axons, but not cell bodies, are activated by electrical stimulation in cortical gray matter. I. Evidence from chronaxie measurements," Exp. Brain Res., 118(4) (Feb. 1998), pp. 477-488.
Nowak, LG., et al., "Axons, but not cell bodies, are activated by electrical stimulation in cortical gray matter. II. Evidence from selective inactivation of cell bodies and axon initial segments," Exp. Brain Res., 118(4) (Feb. 1998), pp. 489-500.
O'Suilleabhain, PE., et al., "Tremor response to polarity, voltage, pulsewidth and frequency of thalamic stimulation," Neurology, 60(5) (Mar. 11, 2003), pp. 786-790.
Pierpaoli, C., et al., "Toward a quantitative assessment of diffusion anisotropy," Magn Reson Med., 36(6) (Dec. 1996), pp. 893-906.
Plonsey, R., et al., "Considerations of quasi-stationarity in electrophysiological systems, " Bull Math Biophys., 29(4) (Dec. 1967), pp. 657-664.
Ranck, J B., "Specific impedance of rabbit cerebral cortex," Exp. Neurol., vol. 7 (Feb. 1963), pp. 144-152.
Ranck, J B., et al., "The Specific impedance of the dorsal columns of the cat: an anisotropic medium," Exp. Neurol., 11 (Apr. 1965), pp. 451-463.
Ranck, J B., "Which elements are excited in electrical stimulation of mammalian central nervous system: a review," Brain Res., 98(3) (Nov. 21, 1975), pp. 417-440.
Rattay, F., et al., "A model of the electrically excited human cochlear neuron. I. Contribution of neural substructures to the generation and propagation of spikes," Hear Res., 153(1-2) (Mar. 2001), pp. 43-63.
Rattay, F., "A model of the electrically excited human cochlear neuron. II. Influence of the three-dimensional cochlear structure on neural excitability," Hear Res., 153(1-2) (Mar. 2001), pp. 64-79.
Rattay, F., "Arrival at Functional Electrostimulation by modelling of fiber excitation," Proceedings of the Ninth annual Conference of the IEEE Engineering in Medicine and Biology Society (1987), pp. 1459-1460.
Rattay, F., "The influence of intrinsic noise can preserve the temporal fine structure of speech signals in models of electrically stimulated human cochlear neurones," Journal of Physiology, Scientific Meeting of the Physiological Society, London, England, UK Apr. 19-21, 1999 (Jul. 1999), p. 170P.
Rizzone, M., et al., "Deep brain stimulation of the subthalamic nucleus in Parkinson's disease: effects of variation in stimulation parameters," J. Neurol. Neurosurg. Psychiatry., 71(2) (Aug. 2001), pp. 215-219.
Saint-Cyr, J. A., et al., "Localization of clinically effective stimulating electrodes in the human subthalamic nucleus on magnetic resonance imaging," J. Neurosurg., 87(5) (Nov. 2002), pp. 1152-1166.
Sances, A., et al., "In Electroanesthesia: Biomedical and Biophysical Studies," A Sances and SJ Larson, Eds., Academic Press, NY (1975), pp. 114-124.
Sl. Jean, P., et al., "Automated atlas integration and interactive three-dimensional visualization tools for planning and guidance in functional neurosurgery," IEEE Transactions on Medical Imaging, 17(5) (1998), pp. 672-680.
Starr, P.A., et al., "Implantation of deep brain stimulators into the subthalamic nucleus: technical approach and magnetic resonance imaging-verified lead locations," J. Neurosurg., 97(2) (Aug. 2002), pp. 370-387.
Sterio, D., et al., "Neurophysiological refinement of subthalamic nucleus targeting," Neurosurgery, 50(1) (Jan. 2002), pp. 58-69.
Struijk, J. J., et al., "Excitation of dorsal root fibers in spinal cord stimulation: a theoretical study," IEEE Transactions on Biomedical Engineering, 40(7) (Jul. 1993), pp. 632-639.
Struijk, J J., et al., "Recruitment of dorsal column fibers in spinal cord stimulation: influence of collateral branching," IEEE Transactions on Biomedical Engineering, 39(9) (Sep. 1992), pp. 903-912.
Tamma, F., et al., "Anatomo-clinical correlation of intraoperative stimulation-induced side effects during HF-DBS of the subthalamic nucleus," Neurol Sci., vol. 23 (Suppl 2) (2002), pp. 109-110.
Tarler, M., et al., "Comparison between monopolar and tripolar configurations in chronically implanted nerve cuff electrodes," IEEE 17th Annual Conference Engineering in Medicine and Biology Society, vol. 2 (1995), pp. 1093-1109.
Testerman, Roy L., "Coritical response to callosal stimulation: A model for determining safe and efficient stimulus parameters," Annals of Biomedical Engineering, 6(4) (1978), pp. 438-452.
Tuch, D.S., et al., "Conductivity mapping of biological tissue using diffusion MRI," Ann NY Acad Sci., 888 (Oct. 30, 1999), pp. 314-316.
Tuch, D.S., et al., "Conductivity tensor mapping of the human brain using diffusion tensor MRI," Proc Nall Acad Sci USA, 98(20) (Sep. 25, 2001), pp. 11697-11701.
Veraart, C., et al., "Selective control of muscle activation with a multipolar nerve cuff electrode," IEEE Transactions on Biomedical Engineering, 40(7) (Jul. 1993), pp. 640-653.
Vercueil, L., et al., "Deep brain stimulation in the treatment of severe dystonia," J. Neurol., 248(8) (Aug. 2001 ), pp. 695-700.
Vilalte, "Circuit Design of the Power-on-Reset," Apr. 2000, pp. 1-25.

(56) References Cited

OTHER PUBLICATIONS

Vitek, J. L., "Mechanisms of deep brain stimulation: excitation or inhibition," Mov. Disord., vol. 17 (Suppl. 3) (2002), pp. 69-72.
Voges, J., et al., "Bilateral high-frequency stimulation in the subthalamic nucleus for the treatment of Parkinson disease: correlation of therapeutic effect with anatomical electrode position," J. Neurosurg., 96(2) (Feb. 2002), pp. 269-279.
Wakana, S., et al., "Fiber tract-based atlas of human white matter anatomy," Radiology, 230(1) (Jan. 2004), pp. 77-87.
Alexander, DC., et al., "Spatial transformations of diffusion tensor magnetic resonance images," IEEE Transactions on Medical Imaging, 20 (11), (2001), pp. 1131-1139.
Wu, Y. R., et al., "Does Stimulation of the GPi control dyskinesia by activating inhibitory axons?," Mov. Disord., vol. 16 (2001), pp. 208-216.
Yelnik, J., et al., "Localization of stimulating electrodes in patients with Parkinson disease by using a three-dimensional atlas-magnetic resonance imaging coregistration method," J Neurosurg., 99(1) (Jul. 2003), pp. 89-99.
Yianni, John, et al., "Globus pallidus internus deep brain stimulation for dystonic conditions: a prospective audit," Mov. Disord., vol. 18 (2003), pp. 436-442.
Zonenshayn, M., et al., "Comparison of anatomic and neurophysiological methods for subthalamic nucleus targeting," Neurosurgery, 47(2) (Aug. 2000), pp. 282-294.
Voghell et al., "Programmable Current Source Dedicated to Implantable Microstimulators" ICM '98 Proceedings of the Tenth International Conference, pp. 67-70.
Butson, Christopher R., et al., "Patient-specific analysis of the volume of tissue activated during deep brain stimulation", NeuroImage. vol. 34. (2007),661-670.
Adler, DE., et al., "The tentorial notch: anatomical variation, morphometric analysis, and classification in 100 human autopsy cases," J. Neurosurg., 96(6), (Jun. 2002), pp. 1103-1112.
Jones et al., "An Advanced Demultiplexing System for Physiological Stimulation", IEEE Transactions on Biomedical Engineering, vol. 44 No. 12 Dec. 1997, pp. 1210-1220.
Zhang, Y., et al., "Atlas-guided tract reconstruction for automated and comprehensive examination of the white matter anatomy," Neuroimage 52(4) (2010), pp. 1289-1301.
""BioPSE" The Biomedical Problem Solving Environment", htt12://www.sci.utah.edu/cibc/software/index.html, MCRR Center for Integrative Biomedical Computing,(2004).
Andrews, R. J., "Neuroprotection trek—the next generation: neuromodulation I. Techniques—deep brain stimulation, vagus nerve stimulation, and transcranial magnetic stimulation.", Ann NY Acad Sci. 993. (May 2003), 1-13.
Carnevale, N.T. et al., "The Neuron Book," Cambridge, UK: Cambridge University Press (2006), 480 pages.
Chaturvedi: "Development of Accurate Computational Models for Patient-Specific Deep Brain Stimulation," Electronic Thesis or Dissertation, Jan. 2012, 162 pages.
Chaturvedi, A. et al.: "Patient-specific models of deep brain stimulation: Influence of field model complexity on neural activation predictions." Brain Stimulation, Elsevier, Amsterdam, NL, vol. 3, No. Apr. 2, 2010, pp. 65-77.
Frankemolle, et al., "Reversing cognitive-motor impairments in Parkinson's disease patients using a computational modeling approach to deep brain stimulation programming," Brian 133 (2010), pp. 746-761.
McIntyre, C.C., et al., "Modeling the excitablitity of mammalian nerve fibers: influence of afterpotentials on the recovery cycle," J Neurophysiol, 87(2) (Feb. 2002), pp. 995-1006.
Peterson, et al., "Predicting myelinated axon activation using spatial characteristics of the extracellular field," Journal of Neural Engineering, 8 (2011), 12 pages.
Warman, et al., "Modeling the Effects of Electric Fields on nerver Fibers; Dermination of Excitation Thresholds," IEEE Transactions on Biomedical Engineering, vol. 39, No. 12 (Dec. 1992), pp. 1244-1254.
Wesselink, et al., "Analysis of Current Density and Related Parameters in Spinal Cord Stimulation," IEEE Transactions on Rehabilitation Engineering, vol. 6, No. Jun. 2, 1998, pp. 200-207.
Andrews, R. J., "Neuroprotection trek—the next generation: neuromodulation II. Applications—epilepsy, nerve regeneration, neurotrophins.", Ann NY Acad Sci. 993 (May 2003), 14-24.
Astrom, M. , et al., "The effect of cystic cavities on deep brain stimulation in the basal ganglia: a simulation-based study", J Neural Eng., 3(2), (Jun. 2006).132-8.
Bazin et al., "Free Software Tools for Atlas-based Volumetric Neuroimage Analysis", Proc. SPIE 5747, Medical Imaging 2005: Image Processing, 1824 May 5, 2005.
Back, C. , et al., "Postoperative Monitoring of the Electrical Properties of Tissue and Electrodes in Deep Brain Stimulation", Neuromodulation, 6(4), (Oct. 2003 ),248-253.
Baker, K. B., et al., "Evaluation of specific absorption rate as a dosimeter of MRI-related implant heating", J Magn Reson Imaging., 20(2), (Aug. 2004),315-20.
Brown, J. "Motor Cortex Stimulation," Neurosurgical Focus ( Sep. 15, 2001) 11(3):E5.
Budai et al., "Endogenous Opioid Peptides Acting at m-Opioid Receptors in the Dorsal Horn Contribute to Midbrain Modulation of Spinal Nociceptive Neurons," Journal of Neurophysiology (1998) 79(2): 677-687.
Cesselin, F. "Opioid and anti-opioid peptides," Fundamental and Clinical Pharmacology (1995) 9(5): 409-33 (Abstract only).
Rezai et al., "Deep Brain Stimulation for Chronic Pain" Surgical Management of Pain, Chapter 44 pp. 565-576 (2002).
Xu, MD., Shi-Ang, article entitled "Comparison of Half-Band and Full-Band Electrodes for Intracochlear Electrical Stimulation", Annals of Otology, Rhinology & Laryngology (Annals of Head & Neck Medicine & Surgery), vol. 102 (5) pp. 363-367 May 1993.
Bedard, C. , et al., "Modeling extracellular field potentials and the frequency-filtering properties of extracellular space", Biophys J .. 86(3). (Mar. 2004),1829-42.
Benabid, A. L., et al., "Future prospects of brain stimulation", Neurol Res.,22(3), (Apr. 2000),237-46.
Brummer, S. B., et al., "Electrical Stimulation with Pt Electrodes: II—Estimation of Maximum Surface Redox (Theoretical Non-Gassing) Limits", IEEE Transactions on Biomedical Engineering, vol. BME-24, Issue 5, (Sep. 1977),440-443.
Butson, Christopher R., et al., "Deep Brain Stimulation of the Subthalamic Nucleus: Model-Based Analysis of the Effects of Electrode Capacitance on the Volume of Activation", Proceedings of the 2nd International IEEE EMBS, (Mar. 16-19, 2005),196-197.
Mcintyre, Cameron C., et al., "Cellular effects of deep brain stimulation: model-based analysis of activation and inhibition," J Neurophysiol, 91(4) (Apr. 2004), pp. 1457-1469.
Chaturvedi, A., et al., "Subthalamic Nucleus Deep Brain Stimulation: Accurate Axonal Threshold Prediction with Diffusion Tensor Based Electric Field Models", Engineering in Medicine and Biology Society, 2006. EMBS' 06 28th Annual International Conference of the IEEE, IEEE, Piscataway, NJ USA, Aug. 30, 2006.
Butson, Christopher et al., "Predicting the Effects of Deep Brain Stimulation with Diffusion Tensor Based Electric Field Models" Jan. 1, 2001, Medical Image Computing and Computer-Assisted Intervention-Mic CAI 2006 Lecture Notes in Computer Science; LNCS, Springer, Berlin, DE.
Butson, C. R., et al., "Deep brainstimulation interactive visualization system", Society for Neuroscience vol. 898.7 (2005),.
Hodaie, M., et al., "Chronic anterior thalamus stimulation for intractable epilepsy," Epilepsia, 43(6) (Jun. 2002), pp. 603-608.
Hoekema, R., et al., "Multigrid solution of the potential field in modeling electrical nerve stimulation," Comput Biomed Res., 31(5) (Oct. 1998), pp. 348-362.
Holsheimer, J., et al., "Identification of the target neuronal elements in electrical deep brain stimulation," Eur J Neurosci., 12(12) (Dec. 2000), pp. 4573-4577.
Jezernik, S., et al., "Neural network classification of nerve activity recorded in a mixed nerve," Neurol Res., 23(5) (Jul. 2001), pp. 429-434.

(56) References Cited

OTHER PUBLICATIONS

Jones, DK., et al., "Optimal strategies for measuring diffusion in anisotropic systems by magnetic resonance imaging," Magn. Reson. Med., 42(3) (Sep. 1999), pp. 515-525.
Krack, P., et al., "Postoperative management of subthalamic nucleus stimulation for Parkinson's disease," Mov. Disord., vol. 17(suppl 3) (2002), pp. 188-197.
Le Bihan, D., et al., "Diffusion tensor imaging: concepts and applications," J Magn Reson Imaging, 13(4) (Apr. 2001), pp. 534-546.
Lee, D. C., et al., "Extracellular electrical stimulation of central neurons: quantitative studies," In: Handbook of neuroprosthetic methods, WE Finn and PG Lopresti (eds) CRC Press (2003), pp. 95-125.
Levy, AL., et al., "An Internet-connected, patient-specific, deformable brain atlas integrated into a surgical navigation system," J Digit Imaging, 10(3 Suppl 1) (Aug. 1997), pp. 231-237.
Liu, Haiying, et al., "Intra-operative MR-guided DBS implantation for treating PD and ET," Proceedings of SPIE vol. 4319, Department of Radiology & Neurosurgery, University of Minnesota, Minneapolis, MN 55455 (2001), pp. 272-276.
Mcintyre, C. C., et al., "Extracellular stimulation of central neurons: influence of stimulus waveform and frequency on neuronal output," J. Neurophysiol., 88(4), (Oct. 2002), pp. 1592-1604.
Mcintyre, C. C., et al., "Microstimulation of spinal motoneurons: a model study," Proceedings of the 19th Annual International Conference of the IEEE Engineering in Medicine and Biology society, vol. 5, (1997), pp. 2032-2034.
Mcintyre, Cameron C., et al., "Model-based Analysis of deep brain stimulation of the thalamus," Proceedings of the Second joint EMBS/BM ES Conference, vol. 3, Annual Fall Meeting of the Biomedical Engineering Society (Cal. No. 02CH37392) IEEEPiscataway, NJ (2002), pp. 2047-2048.
Mcintyre, C. C., et al., "Model-based design of stimulus trains for selective microstimulation of targeted neuronal populations," Proceedings of the 23rd Annual International Conference of the IEEE Engineering in Medicine and Biology Society, vol. 1 (2001), pp. 806-809.
Mcintyre, C. C., et al., Model-based design of stimulus waveforms for selective microstimulation in the central nervous system,, Proceedings of the First Joint [Engineering in Medicine and Biology, 1999. 21st Annual Conf. and the 1999 Annual FallMeeting of the Biomedical Engineering Soc.] BM ES/EMBS Conference, vol. 1 (1999), p. 384.
Mcintyre, Cameron C., et al., "Modeling the excitability of mammalian nerve fibers: influence of aflerpotentials on the recovery cycle," J Neurophysiol, 87(2) (Feb. 2002), pp. 995-1006.
Mcintyre, Cameron C., et al., "Selective microstimulation of central nervous system neurons," Annals of biomedical engineering, 28(3) (Mar. 2000), pp. 219-233.
Mcintyre, C. C., et al., "Sensitivity analysis of a model of mammalian neural membrane," Biol Cybern., 79(1) (Jul. 1998), pp. 29-37.
Mcintyre, Cameron C., et al., "Uncovering the mechanism(s) of action of deep brain stimulation: activation, inhibition, or both," Clin Neurophysiol, 115(6) (Jun. 2004), pp. 1239-1248.
Mcintyre, Cameron C., et al., "Uncovering the mechanisms of deep brain stimulation for Parkinson's disease through functional imaging, neural recording, and neural modeling," Crit Rev Biomed Eng., 30(4-6) (2002), pp. 249-281.
Mouine et al. "Multi-Strategy and Multi-Algorithm Cochlear Prostheses", Biomed. Sci. Instrument, 2000; 36:233-238.

* cited by examiner

| Background Ratio | Charge | % Target Volume Stimulated |
|---|---|---|
| 0.0352 | 300 | 20.7 |
| 0.0481 | 300 | 20.7 |
| 0.0657 | 288 | 20.9 |
| 0.0899 | 276 | 20.7 |

SYSTEMS AND METHODS FOR USING COST PARAMETERS FOR PROGRAMMING ELECTRICAL STIMULATION

CROSS-REFERENCE TO RELATED APPLICATIONS

This application claims the benefit under 35 U.S.C. § 119(e) of U.S. Provisional Patent Application Ser. No. 63/320,176, filed Mar. 15, 2022, and U.S. Provisional Patent Application Ser. No. 63/313,710, filed Feb. 24, 2022, both of which are incorporated herein by reference.

FIELD

The present invention is directed to the area of implantable electrical stimulation systems and methods of making and using the systems. The present invention is also directed to systems and methods for identifying and using cost parameters for programming electrical stimulation.

BACKGROUND

Implantable electrical stimulation systems have proven therapeutic in a variety of diseases, disorders, and conditions. For example, spinal cord stimulation systems have been used as a therapeutic modality for the treatment of chronic pain syndromes. Peripheral nerve stimulation has been used to treat chronic pain syndrome and incontinence, with a number of other applications under investigation. Functional electrical stimulation systems have been applied to restore some functionality to paralyzed extremities in spinal cord injury patients. Stimulation of the brain, such as deep brain stimulation, can be used to treat a variety of diseases, disorders, conditions, and symptoms.

Stimulators have been developed to provide therapy for a variety of treatments. A stimulator can include a control module (with a pulse generator), at least one lead, and an array of stimulator electrodes on each lead. The stimulator electrodes are in contact with or near the nerves, muscles, or other tissue to be stimulated. The pulse generator in the control module generates electrical pulses that are delivered by the electrodes to body tissue.

BRIEF SUMMARY

One aspect is a method for programming an electrical stimulation system including at least one implantable electrical stimulation lead including a plurality of electrodes. The method includes receiving a target and a location of the at least one implantable electrical stimulation lead; receiving at least one stimulation criterion; for each of the at least one stimulation criterion, identifying one or more values of a cost parameter that meet the stimulation criterion, wherein the cost parameter includes a ratio of a cost of stimulating at least one defined region of tissue over a benefit of stimulating a region of the target; and providing at least one of the one or more values of the cost parameter that meet the at least one stimulation criterion to a user or the electrical stimulation system to assist in programming the electrical stimulation system.

Another aspect is an electrical stimulation system that includes at least one implantable electrical stimulation lead including a plurality of electrodes; a control unit coupled to the at least one implantable electrical stimulation lead and configured for generating electrical stimulation for delivery through the at least one implantable electrical stimulation lead; and a processor configured to identify stimulation parameters for programming of the control unit to generate the electrical stimulation. The processor is configured to perform actions including receiving a target and a location of the at least one implantable electrical stimulation lead; receiving at least one stimulation criterion; for each of the at least one stimulation criterion, identifying one or more values of a cost parameter that meet the stimulation criterion, wherein the cost parameter includes a ratio of a cost of stimulating at least one defined region of tissue over a benefit of stimulating a region of the target; and providing at least one of the one or more values of the cost parameter that meet the at least one stimulation criterion to a user or the electrical stimulation system to assist in programming the electrical stimulation system.

A further aspect is a non-transitory computer-readable medium having computer executable instructions stored thereon that, when executed by at least one processor, cause the at least one processor to perform actions including receiving a target and a location of the at least one implantable electrical stimulation lead; receiving at least one stimulation criterion; for each of the at least one stimulation criterion, identifying one or more values of a cost parameter that meet the stimulation criterion, wherein the cost parameter includes a ratio of a cost of stimulating at least one defined region of tissue over a benefit of stimulating a region of the target; and providing at least one of the one or more values of the cost parameter that meet the at least one stimulation criterion to a user or the electrical stimulation system to assist in programming the electrical stimulation system.

In at least some aspects, the at least one stimulation criterion is at least two stimulation criteria and the method further includes identifying, from the identified one or more values of the cost parameter, at least one overlap value of the cost parameter that meets each of the at least two stimulation criterion, wherein providing at least one of the one or more values of the cost parameter includes providing the at least one overlap value to a user or the electrical stimulation system to assist in programming the electrical stimulation system. In at least some aspects, the method or actions further includes providing a message to a user or the electrical stimulation system when no overlap value is identified.

In at least some aspects, the method or actions further includes receiving a user selection of a one of the one or more values of the cost parameter that meet the at least one stimulation criterion. In at least some aspects, the cost parameter includes a) a ratio of a cost of stimulating a volume of tissue around the at least one implantable electrical stimulation lead over the benefit of stimulating a volume of the target region; b) a ratio of a cost of stimulating a volume of tissue outside of the target region over the benefit of stimulating the volume of the target region; or c) a ratio of a cost of stimulating a volume of a side effect or avoidance region over the benefit of stimulating the volume of the target region.

In at least some aspects, the method or actions further includes receiving at least one side effect or avoidance region. In at least some aspects, the identifying one or more values of the cost parameter includes, for each of the at least one stimulation criterion, comparing a plurality of stimulation fields to the stimulation criterion and determining which of the stimulation fields meet the stimulation criterion, wherein each of the stimulation fields corresponds to an estimated volume of stimulation for a particular set of stimulation parameters corresponding the stimulation field, wherein each of the stimulation fields has a value of the cost parameter determined from the estimated volume of stimulation for the particular set of stimulation parameters.

In at least some aspects, the method or actions further includes programming the electrical stimulation system utilizing a one of the one or more values of the cost parameter that meet the at least one stimulation criterion. In at least some aspects, the method or actions further includes stimulating a patient using the at least one implantable electrical stimulation lead and the programming of the electrical stimulation system utilizing the one of the one or more values of the cost parameter that meet the at least one stimulation criterion.

In at least some aspects, the method or actions further includes obtaining or receiving at least one clinical response for the stimulation; altering a stimulation parameter; performing a second stimulation of the patient using the altered stimulation parameter; obtaining or receiving at least one clinical response for the second stimulation; and querying whether the at least one clinical response for the second stimulation meets a goal for each of one or more desired benefits without generating a side effect above a threshold value.

In at least some aspects, the method or actions further includes, when a result of the querying is negative, i) altering the one of the one or more values of the cost parameter that meet the at least one stimulation criterion to provide an altered value of the cost parameter; ii) programming the electrical stimulation system utilizing the altered value of the cost parameter; iii) performing a third stimulation of the patient using the at least one implantable electrical stimulation lead and the programming of the electrical stimulation system utilizing the altered value of the cost parameter; iv) obtaining or receiving at least one clinical response for the third stimulation; v) querying whether the at least one clinical response for the third stimulation meets a target for each of one or more desired benefits without generating a side effect above a threshold value; and repeating steps i)-v) when a result of the querying in step v) is negative.

In at least some aspects, the method or actions further includes forming a map of the at least one clinical response for each of the first stimulation, the second stimulation, and each instance of the third stimulation, wherein the map has a first axis corresponding the cost parameter and a second axis corresponding to a second cost parameter.

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

For a better understanding of the present invention, reference will be made to the following Detailed Description, which is to be read in association with the accompanying drawings, wherein.

DETAILED DESCRIPTION

Figure 1:
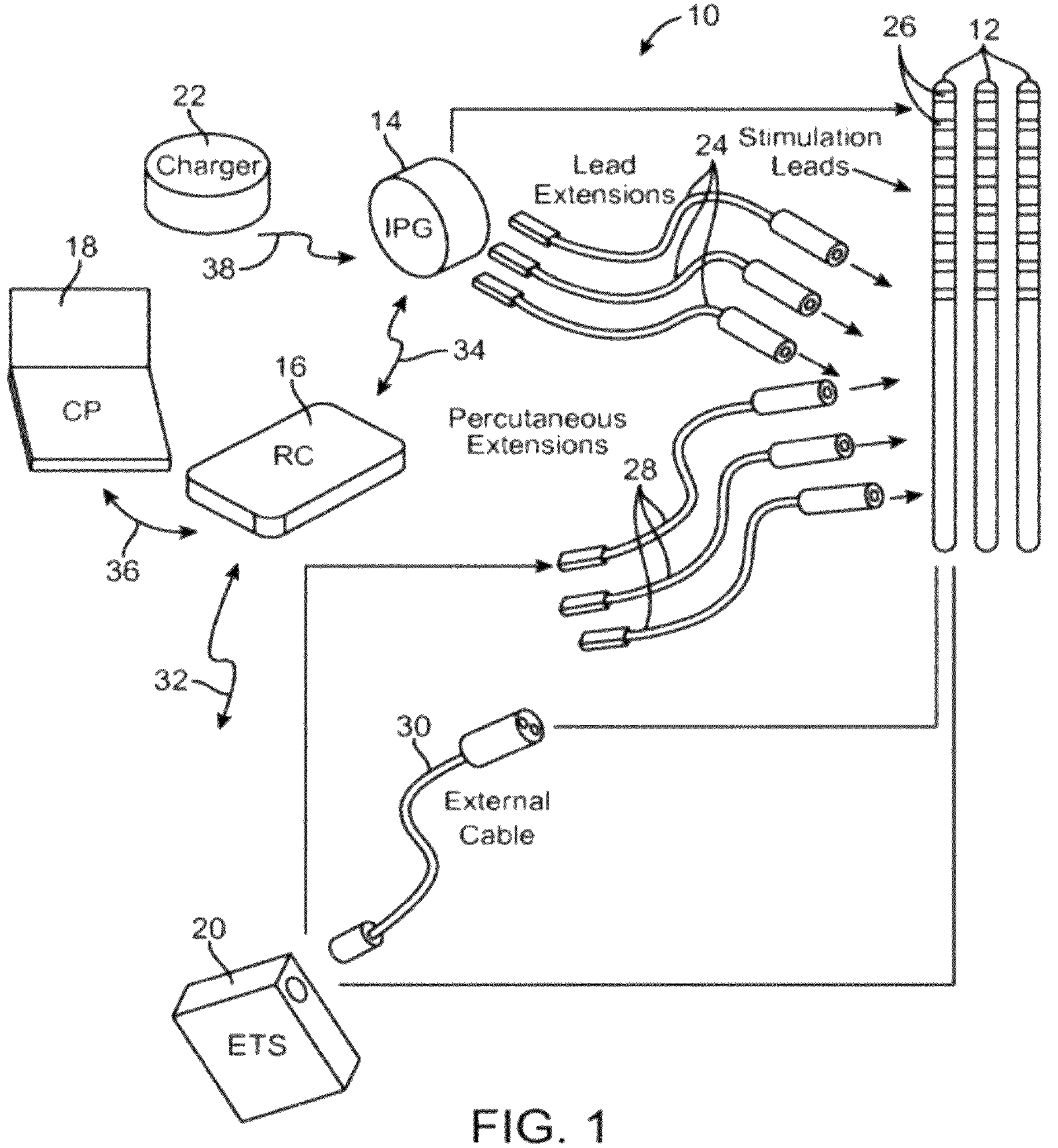
FIG. 1 is a schematic view of one embodiment of an electrical stimulation system.

The present invention is directed to the area of implantable electrical stimulation systems and methods of making and using the systems. The present invention is also directed to systems and methods for identifying and using cost parameters for programming electrical stimulation.

Suitable implantable electrical stimulation systems include, but are not limited to, a least one lead with at least one electrode disposed on a distal end portion of the lead and at least one terminal disposed on at least one proximal end portion of the lead. Leads include, for example, percutaneous leads, paddle leads, cuff leads, or any other arrangement of electrodes on a lead. Examples of electrical stimulation systems with leads are found in, for example, U.S. Pat. Nos. 6,181,969; 6,516,227; 6,609,029; 6,609,032; 6,741,892; 7,244,150; 7,450,997; 7,672,734; 7,761,165; 7,783,359; 7,792,590; 7,809,446; 7,949,395; 7,974,706; 8,175,710; 8,224,450; 8,271,094; 8,295,944; 8,364,278; 8,391,985; and 8,688,235; and U.S. Patent Applications Publication Nos. 2007/0150036; 2009/0187222; 2009/0276021; 2010/0076535; 2010/0268298; 2011/0005069; 2011/0004267; 2011/0078900; 2011/0130817; 2011/0130818; 2011/0238129; 2011/0313500; 2012/0016378; 2012/0046710; 2012/0071949; 2012/0165911; 2012/0197375; 2012/0203316; 2012/0203320; 2012/0203321; 2012/0316615; 2013/0105071; and 2013/0197602, all of which are incorporated by reference. In the discussion below, a percutaneous lead will be exemplified, but it will be understood that the methods and systems described herein are also applicable to paddle leads and other leads.

A lead for electrical stimulation (for example, deep brain or spinal cord stimulation) includes stimulation electrodes that can be ring electrodes, segmented electrodes that extend only partially around the circumference of the lead, or any other type of electrode, or any combination thereof. The segmented electrodes can be provided in sets of electrodes, with each set having electrodes circumferentially distributed about the lead at a particular longitudinal position or across a particular longitudinal region. For illustrative purposes, the leads are described herein relative to use for deep brain stimulation, but it will be understood that any of the leads can be used for applications other than deep brain stimulation, including spinal cord stimulation, peripheral nerve stimulation, or stimulation of other nerves, muscles, and tissues. In particular, stimulation may stimulate specific targets. Examples of such targets include, but are not limited to, the subthalamic nucleus (STN), the internal segment of the globus pallidus (GPi), the ventral intermediate nucleus of the thalamus, the external segment of the globus pallidus (GPe), and the like. In at least some embodiments, an anatomical structure is defined by its physical structure and a physiological target is defined by its functional attributes. In at least some embodiments, the lead may be positioned at least partially within the target, but in other embodiments, the lead may be near, but not inside, the target. The stimulation of tissue can include, but is not limited to, one or more of activation, inhibition, depression, or other modulation of the stimulated tissue.

Turning to FIG. 1, one embodiment of an electrical stimulation system 10 includes at least one stimulation lead 12 and an implantable pulse generator (IPG) 14. The system 10 can also include at least one of an external remote control (RC) 16, a clinician's programmer (CP) 18, an external trial stimulator (ETS) 20, or an external charger 22.

The IPG 14 is physically connected, optionally via at least one lead extension 24, to the stimulation lead(s) 12. Each lead carries multiple electrodes 26 arranged in an array. The IPG 14 includes pulse generation circuitry that delivers electrical stimulation energy in the form of, for example, a pulsed electrical waveform (i.e., a temporal series of electrical pulses) to the electrode array 26 in accordance with a set of stimulation parameters. The IPG 14 can be implanted into a patient's body, for example, below the patient's clavicle area or within the patient's buttocks or abdominal cavity. The IPG 14 can have eight stimulation channels which may be independently programmable to control the magnitude of the current stimulus from each channel. In at least some embodiments, the IPG 14 can have more or fewer than eight stimulation channels (for example, 4, 6, 16, 32, or more stimulation channels). The IPG 14 can have one, two, three, four, or more connector ports, for receiving the terminals of the leads.

The ETS 20 may also be physically connected, optionally via the percutaneous lead extensions 28 and external cable 30, to the stimulation leads 12. The ETS 20, which may have similar pulse generation circuitry as the IPG 14, also delivers electrical stimulation energy in the form of, for example, a pulsed electrical waveform to the electrode array 26 in accordance with a set of stimulation parameters. One difference between the ETS 20 and the IPG 14 is that the ETS 20 is often a non-implantable device that is used on a trial basis after the neurostimulation leads 12 have been implanted and prior to implantation of the IPG 14, to test functioning of the system or the responsiveness of the stimulation that is to be provided. Any functions described herein with respect to the IPG 14 can likewise be performed with respect to the ETS 20.

The RC 16 may be used to telemetrically communicate with or control the IPG 14 or ETS 20 via a uni- or bi-directional wireless communications link 32. Once the IPG 14 and neurostimulation leads 12 are implanted, the RC 16 may be used to telemetrically communicate with or control the IPG 14 via a uni- or bi-directional communications link 34. Such communication or control allows the IPG 14 to be turned on or off and to be programmed with different stimulation parameter sets. The IPG 14 may also be operated to modify the programmed stimulation parameters to actively control the characteristics of the electrical stimulation energy output by the IPG 14. The CP 18 allows a user, such as a clinician, the ability to program stimulation parameters for the IPG 14 and ETS 20 in the operating room and in follow-up sessions.

The CP 18 may perform this function by indirectly communicating with the IPG 14 or ETS 20, through the RC 16, via a wireless communications link 36. Alternatively, the CP 18 may directly communicate with the IPG 14 or ETS 20 via a wireless communications link (not shown). The stimulation parameters provided by the CP 18 are also used to program the RC 16, so that the stimulation parameters can be subsequently modified by operation of the RC 16 in a stand-alone mode (i.e., without the assistance of the CP 18).

For purposes of brevity, the details of the RC 16, CP 18, ETS 20, and external charger 22 will not be further described herein. Details of exemplary embodiments of these devices are disclosed in U.S. Pat. No. 6,895,280, which is expressly incorporated herein by reference. Other examples of electrical stimulation systems can be found at U.S. Pat. Nos. 6,181,969; 6,516,227; 6,609,029; 6,609,032; 6,741,892; 7,949,395; 7,244,150; 7,672,734; and 7,761,165; 7,974,706; 8,175,710; 8,224,450; and 8,364,278; and U.S. Patent Application Publication No. 2007/0150036, as well as the other references cited above, all of which are incorporated by reference.

Figure 2:
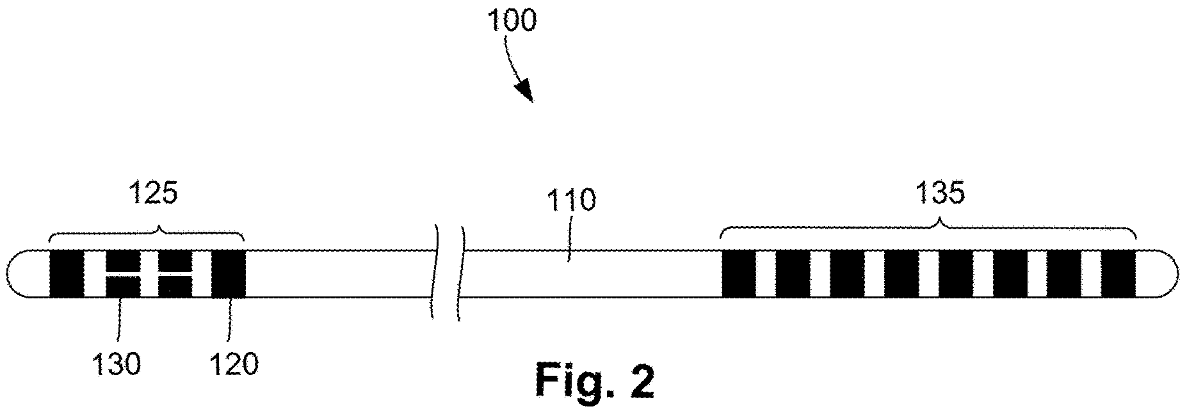
FIG. 2 is a schematic side view of one embodiment of an electrical stimulation lead.

FIG. 2 illustrates one embodiment of a lead 100 with electrodes 125 disposed at least partially about a circumference of the lead 100 along a distal end portion of the lead 100 and terminals 135 disposed along a proximal end portion of the lead 100. The lead 100 can be implanted near or within the desired portion of the body to be stimulated such as, for example, the brain, spinal cord, or other body organs or tissues.

Stimulation electrodes may be disposed on the circumference of the lead 100 to stimulate the target neurons. Stimulation electrodes may be ring shaped so that current projects from each electrode radially from the position of the electrode along a length of the lead 100. In the embodiment of FIG. 2, two of the electrodes 125 are ring electrodes 120. Ring electrodes typically do not enable stimulus current to be directed from only a limited angular range around a lead. Segmented electrodes 130, however, can be used to direct stimulus current to a selected angular range around a lead. When segmented electrodes are used in conjunction with an implantable pulse generator that includes multiple independent current sources, current steering can be achieved to more precisely deliver the stimulus to a position around an axis of a lead (i.e., radial positioning around the axis of a lead). To achieve current steering, segmented electrodes can be utilized in addition to, or as an alternative to, ring electrodes.

The lead 100 includes a lead body 110, terminals 135, at least one ring electrode 120, and at least one set of segmented electrodes 130 (or any other combination of electrodes). The lead body 110 can be formed of a biocompatible, non-conducting material such as, for example, a polymeric material. Suitable polymeric materials include, but are not limited to, silicone, polyurethane, polyurea, polyurethane-urea, polyethylene, or the like. Once implanted in the body, the lead 100 may be in contact with body tissue for extended periods of time. In at least some embodiments, the lead 100 has a cross-sectional diameter of no more than 1.5 mm and may be in the range of 0.5 to 1.5 mm. In at least some embodiments, the lead 100 has a length of at least 10 cm and the length of the lead 100 may be in the range of 10 to 70 cm.

The electrodes 125 can be made using a metal, alloy, conductive oxide, or any other suitable conductive biocompatible material. Examples of suitable materials include, but are not limited to, platinum, platinum iridium alloy, iridium, titanium, tungsten, palladium, palladium rhodium, or the like. Preferably, the electrodes 125 are made of a material that is biocompatible and does not substantially corrode under expected operating conditions in the operating environment for the expected duration of use.

Each of the electrodes 125 can either be used or unused (OFF). When an electrode is used, the electrode can be used as an anode or cathode and carry anodic or cathodic current. In some instances, an electrode might be an anode for a period of time and a cathode for a period of time.

Deep brain stimulation leads may include at least one set of segmented electrodes. Segmented electrodes may provide for superior current steering than ring electrodes because target structures in deep brain stimulation are not typically symmetric about the axis of the distal electrode array. Instead, a target may be located on one side of a plane running through the axis of the lead. Through the use of a radially segmented electrode array ("RSEA"), current steering can be performed not only along a length of the lead but also around a circumference of the lead. This provides precise three-dimensional targeting and delivery of the current stimulus to neural target tissue, while potentially avoiding stimulation of other tissue. Examples of leads with segmented electrodes include U.S. Pat. Nos. 8,473,061; 8,571,665; 8,792,993; 9,248,272; 9,775,988; and 10,286,205; U.S. Patent Application Publications Nos. 2010/0268298; 2011/0005069; 2011/0130803; 2011/0130816; 2011/0130817; 2011/0130818; 2011/0078900; 2011/0238129; 2012/0016378; 2012/0046710; 2012/0071949; 2012/0165911; 2012/197375; 2012/0203316; 2012/0203320; 2012/0203321; 2013/0197424; 2013/0197602; 2014/0039587; 2014/0353001; 2014/0358208; 2014/0358209; 2014/0358210; 2015/0045864; 2015/0066120; 2015/0018915; and 2015/0051681, all of which are incorporated herein by reference.

Figure 3:
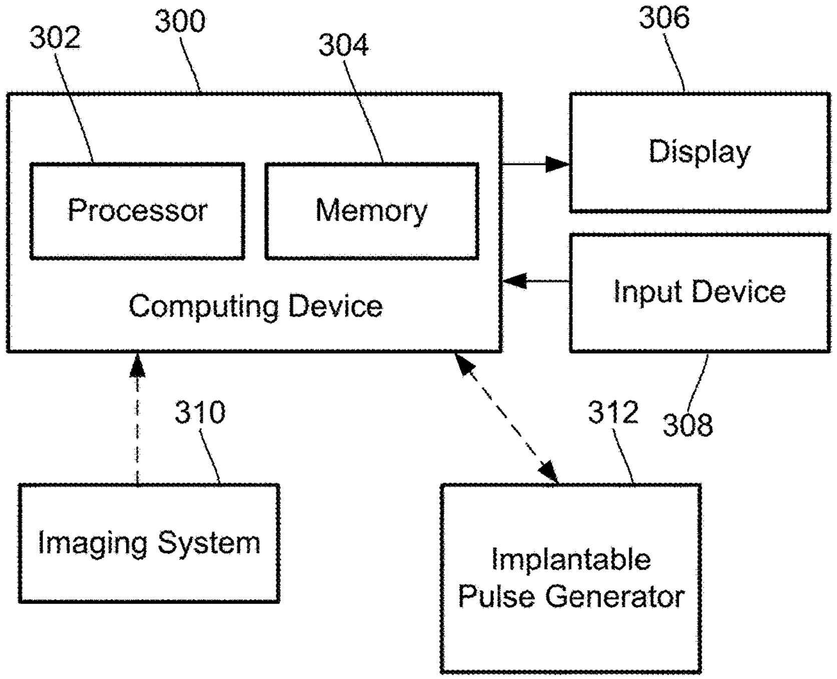
FIG. 3 is a schematic block diagram of one embodiment of a system for automatically aligning brain atlases using clinical responses.

FIG. 3 illustrates one embodiment of a system for practicing the invention. The system can include a computing device 300 or any other similar device that includes a processor 302 and a memory 304, a display 306, an input device 308, and, optionally, an implantable pulse generator 312 (such as IPG 14 of FIG. 1). The system 300 may also optionally include at least one imaging system 310.

The computing device 300 (with or without the display 306 and input device 308) can be the RC 16, CP 18, a computer, tablet, mobile device, any other suitable device for processing information, or any combination thereof. The computing device 300 can be local to the user or can include components that are non-local to the computer including one or both of the processor 302 or memory 304 (or portions thereof). For example, in at least some embodiments, the user may operate a terminal that is connected to a non-local computing device. In other embodiments, the memory can be non-local to the user.

The computing device 300 can utilize any suitable processor 302 including at least one hardware processors that may be local to the user or non-local to the user or other components of the computing device. The processor 302 is configured to execute instructions provided to the processor 302, as described below.

Any suitable memory 304 can be used for the computing device 302. The memory 304 illustrates a type of computer-readable media, namely computer-readable storage media. Computer-readable storage media may include, but is not limited to, nonvolatile, non-transitory, removable, and non-removable media implemented in any method or technology for storage of information, such as computer readable instructions, data structures, program modules, or other data. Examples of computer-readable storage media include RAM, ROM, EEPROM, flash memory, or other memory technology, CD-ROM, digital versatile disks ("DVD") or other optical storage, magnetic cassettes, magnetic tape, magnetic disk storage or other magnetic storage devices, or any other medium which can be used to store the desired information and which can be accessed by a computing device.

Communication methods provide another type of computer readable media; namely communication media. Communication media typically embodies computer-readable instructions, data structures, program modules, or other data in a modulated data signal such as a carrier wave, data signal, or other transport mechanism and include any information delivery media. The terms "modulated data signal," and "carrier-wave signal" includes a signal that has at least one of its characteristics set or changed in such a manner as to encode information, instructions, data, and the like, in the signal. By way of example, communication media includes wired media such as twisted pair, coaxial cable, fiber optics, wave guides, and other wired media and wireless media such as acoustic, RF, infrared, and other wireless media.

The display 306 can be any suitable display device, such as a monitor, screen, display, or the like, and can include a printer. The input device 308 can be, for example, a keyboard, mouse, touch screen, track ball, joystick, voice recognition system, or any combination thereof, or the like.

At least one imaging system 310 can be used including, but not limited to, MM, computed tomography (CT), ultrasound, or other imaging systems. The imaging system 310 may communicate through a wired or wireless connection with the computing device 300 or, alternatively or additionally, a user can provide images from the imaging system 310 using a computer-readable medium or by some other mechanism. The imaging system 310 may be useful for locating the electrical stimulation lead(s) implanted in a patient.

The methods and systems described herein may be embodied in many different forms and should not be construed as limited to the embodiments set forth herein. Accordingly, the methods and systems described herein may take the form of an entirely hardware embodiment, an entirely software embodiment or an embodiment combining software and hardware aspects. Systems referenced herein typically include memory and typically include methods for communication with other devices including mobile devices. Methods of communication can include both wired and wireless (for example, RF, optical, or infrared) communications methods and such methods provide another type of computer readable media; namely communication media. Wired communication can include communication over a twisted pair, coaxial cable, fiber optics, wave guides, or the like, or any combination thereof. Wireless communication can include RF, infrared, acoustic, near field communication, Bluetooth™, or the like, or any combination thereof.

Given the number of electrodes and the possibility of using multiple electrodes together, along with the directionality provided by segmented electrodes, it can be challenging to identify a suitable set of stimulation parameters to treat a disease, disorder, condition, symptom, or the like. The stimulation parameters include the selection of one or more electrodes for delivery of stimulation, the stimulation amplitude and polarity for each selected electrode, pulse width, pulse frequency, and the like. The number of degrees of programming freedom can be daunting. It is, therefore, useful to identify methods and systems that can facilitate programming and identifying suitable stimulation parameters for stimulation programs.

Furthermore, instead of programming individual stimulation parameters, another programming paradigm includes identification of a target and balancing stimulation of the target with, for example, stimulation outside the target or the generation of side effects or other effects of stimulation. For example, increasing the percentage or amount of the target that is stimulated may also increase the volume outside of the target that is stimulated or may increase the side effects resulting from stimulation (for example, by increasing the amount of a side effect (or avoidance) region that is stimulated.) Thus, there may be a need to balance the amount of the target that is stimulated to avoid stimulating non-target regions or producing side effects.

A region of tissue is stimulated when sufficient stimulation energy (which may be in any suitable form, such as a stimulation current or voltage) is provided to the region to generate a physiological response to the stimulation energy. Generally, the amount of energy received by a region of tissue decreases with distance from the source of the energy (e.g., the electrode(s) of the stimulation lead(s) used to deliver the stimulation.) In at least some embodiments, a threshold value corresponds to the minimum amount of stimulation energy necessary to generate the physiological response. In at least some embodiments, the physiological response can be a therapeutic stimulation effect or a side effect.

Stimulation of the tissue produces a stimulation field. The terms "stimulation field" (SF), "stimulation field map" (SFM), "volume of activation" (VOA), or "volume of tissue activated (VTA)" are often used to designate an estimated region of tissue that will be stimulated for a particular set of stimulation parameters. Unless indicated otherwise, these terms are used interchangeably herein. Any suitable method for determining the SF/VOA/SFM/VTA can be used including, but not limited to, those described in, for example, U.S. Pat. Nos. 8,326,433; 8,675,945; 8,831,731; 8,849,632; 8,958,615; and 10,265,528; U.S. Patent Application Publications Nos. 2009/0287272; 2009/0287273; 2012/0314924; 2013/0116744; 2014/0122379; and 2015/0066111, all of which are incorporated herein by reference in their entireties. In at least some embodiments, a system (or other programming arrangement) may have a collection of predetermined stimulation fields which may be contained in, for example, a look-up table, database, or the like. In at least some instances, interpolation or other estimation methods can be used to modify a predetermined stimulation field to provide additional stimulation fields for consideration.

In at least some embodiments, when programming electrical stimulation a user can identify a target which can include one or more target regions. In at least some embodiments, the target or target region can correspond to, for example, a specified anatomical structure, substructure, region, or subregion such as, for example, the substantia nigra, subthalamic nucleus, globus pallidus internus, or the like or any combination thereof. In at least some embodiments, the target or target region can correspond to, for example, a region selected on a model by the user, such as, for example, regions selected by point-and-click (or any other suitable selection mechanism), by drawing on the model, or the like or any combination thereof.

In at least some embodiments, the target or target region may be identified by identifying a disease, disorder, condition, or symptom that is to be treated or by identifying a stimulation outcome or benefit. The target or target region corresponds to an anatomical structure; anatomical substructure; anatomical or functional region or subregion; any other defined region that is associated with the disease, disorder, condition, symptom, stimulation outcome, or stimulation benefit; any region associated with a physiological signal; or one or more regions that have structural or functional connectivity with another region of interest; or the like or any combination thereof.

Any other suitable mechanism for identifying a target or target region can be used. A target having multiple target regions may have those target regions identified using the same method or mechanism or different methods or mechanisms.

In at least some embodiments, the user can identify one or more side effect regions or avoidance regions. Any of the mechanisms for identifying the target can also be used for side effect regions or avoidance regions. In at least some embodiments, one or more side effect regions or avoidance regions may be predefined in a system. In at least some embodiments, such predefined side effect regions or avoidance regions may be widely known or known to a clinician or programmer using the system.

In at least some embodiments, the balancing of the stimulation of the target with other factors such as, for example, stimulation outside the target or the generation of side effects of stimulation can be represented by one or more cost parameters. As an example, stimulation outside the target can be balanced with the amount of the target that is stimulated. The term "background ratio" is used herein for a cost parameter that represents a ratio of the cost for stimulating tissue (either tissue in general or tissue outside the target) over the benefit for stimulating the target. In at least some embodiments, these costs and benefits are based on unit or equal volumes of tissue.

Similarly, stimulation of one or more side effect regions or other regions to be avoided can be balanced with the amount of the target that is stimulated. The terms "avoidance ratio" or "side effects ratio" are used herein for a cost parameter that represents a ratio of the cost for stimulating tissue in one or more side effects or avoidance regions over the benefit for stimulating the target (or a ratio of the cost for stimulating a unit volume of tissue in one or more side effects or avoidance regions over the benefit for stimulating a unit volume of the target.)

Any other suitable cost parameter can be used. For example, a cost parameter can be based on a stimulation parameter, such as amplitude, and represent a cost for increasing (or otherwise altering) the stimulation parameter or the benefit for the increase (or other alteration.) Other costs that can be part of a cost parameter include, for example, increased battery drain associated with higher amplitude or charge delivered.

In at least some embodiments, a user can program, or modify the programming, an electrical stimulation system by selecting or modifying one or more of the cost parameters. The cost parameter(s) can be used by the electrical stimulation system (or other programming arrangement) to generate one or more sets of stimulation parameters (for example, a selection of one or more electrodes and a stimulation amplitude for each selected electrode) for which the corresponding stimulation field(s) meet(s) the cost parameter(s).

In at least some embodiments, the system (or other programming arrangement) can utilize a metric that incorporates one or more cost parameters to evaluate sets of stimulation parameters. Stimulation fields can be compared to the target and, optionally, the side effect or avoidance regions to determine the corresponding value of the metric. One example of a metric, m, is the following:

$$m=v_{target}-(v_{total}*\text{background ratio})-(v_{avoidance}*\text{avoidance ratio})$$

where $v_{target}$ is the volume of the target within the stimulation field, $v_{total}$ is the volume of the stimulation field, $v_{avoidance}$ is the volume of the side effect or avoidance region(s) within the stimulation field, and the background ratio and avoidance ratio are described above. One or more stimulation fields, and the corresponding set of stimulation parameters, can be selected or suggested by the system (or other programming arrangement) based on the corresponding values of the metric.

Figure 4:
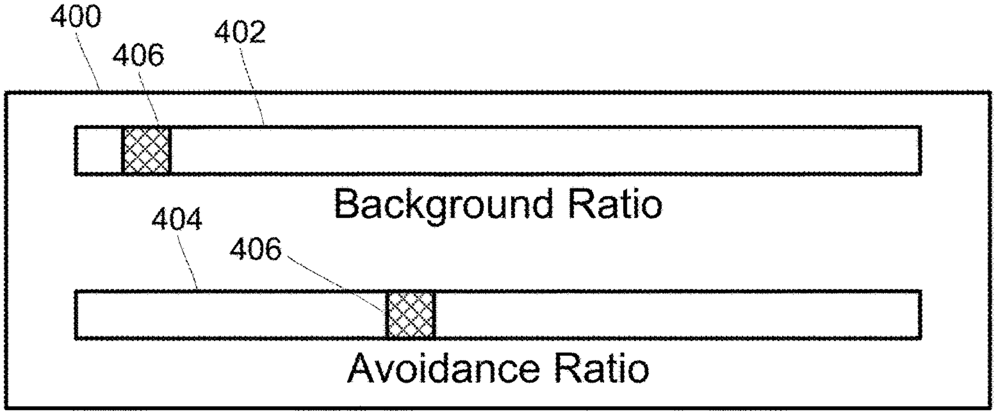
FIG. 4 is a schematic illustration of one embodiment of an interface for selecting values of cost parameters such as Background Ratio and Avoidance Ratio.

As indicated above, a clinician, programmer, or other individual can program, or modify the programming, of an electrical stimulation system by selecting, or modifying, one or more of the cost parameters. FIG. 4 illustrates one embodiment of an interface 400 that includes controls 402, 404 for selecting or modifying one or more cost parameters (for example, a background ratio or an avoidance ratio, respectively) using a slider 406. It will be recognized that any other interface for entering, selecting, or modifying values of a cost parameter can be used. The system (or other programming arrangement) can then determine a set of stimulation parameters based on the selected, or modified, cost parameter(s).

However, the cost parameters, and the effects of modification of a cost parameter, may appear too abstract to a clinician, programmer, or other individual. It may be challenging for the clinician, programmer, or other individual to select, or modify, to obtain a desired stimulation result by modification of one or more cost parameters.

As described herein, a system (or other programming arrangement) or method can utilize one or more user-provided stimulation criterion, which may be more concrete or familiar to a user, clinician, programmer, or other individual, to identify one or more values of the cost parameter(s) that meet the one or more stimulation criterion. This can facilitate the programming of, for example, the electrical stimulation system 10 (FIG. 1) with one or more electrical stimulation leads 12 using the CP 18, RC 16, or another programming arrangement. The electrical stimulation system 10 of FIG. 1 will be used as an example, but it will be understood that the methods and systems described herein can be applied to other electrical stimulation systems.

Figure 5:
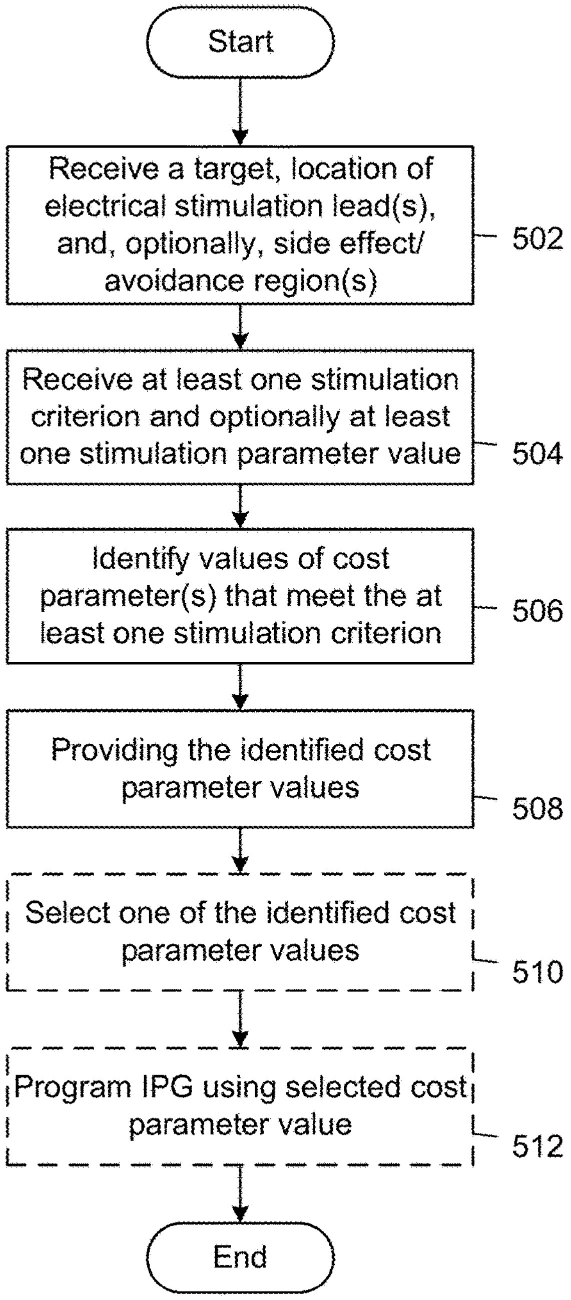
FIG. 5 is a flowchart of one embodiment of a method for programming an electrical stimulation system.

FIG. 5 illustrates one embodiment of a method, which can be implemented in an electrical stimulation system or a programming device or system, for programming an electrical stimulation system that includes at least one implantable electrical stimulation lead. In at least some embodiments, the steps in FIG. 5 can be performed by the CP 18, RC 12, IPG 14, or any other programming device or any combination of these devices.

In step 502, a target and a location of the electrical stimulation lead(s) is received. A target can be single target region or can be multiple target regions that can be individually or collectively determined or selected.

Any suitable method can be used for identifying the target or target regions. In at least some embodiments, the target or target regions can be selected or input by a user (for example, a clinician, programmer, patient, or other suitable individual.) In at least some embodiments, the target or target regions can be selected from a menu containing available target regions. In at least some embodiments, the target or target regions can be selected by entry of a name of the target or target region.

In at least some embodiments, the target or target regions can be determined or selected indirectly by, for example, selecting a disease, disorder, condition, symptom, or the like that is associated with one or more targets or target regions. The target or target region is then determined or selected by the system or user based on the association.

Optionally, in addition to a target, one or more side effect or avoidance regions can be received. Any of the methods described above for identifying the target can also be used for the side effect or avoidance regions.

The location of the electrical stimulation lead(s) can be an actual location or an estimated location. It will be understood that the location of the electrode(s) of the electrical stimulation lead(s) is the same as the location of the electrical stimulation lead(s). The location of the electrical stimulation lead(s) may be provided by the user, by an image or interpretation of an image of the lead(s), by a surgical planning system, or the like that has information regarding the location or planned location of implantation of the lead(s). Any other suitable source for the location of the electrical stimulation lead(s) can be used including any source or user that estimates the location of the electrical stimulation lead(s).

In step 504, at least one stimulation criterion is received from a user (for example, a clinician, programmer, patient, or other suitable individual.) Examples of stimulation criteria include, but are not limited to, threshold values (e.g., minimum value or maximum value or both to provide a range) for one or more of the following: total charge injected into the tissue, charge injected into the tissue per stimulation pulse or period, total energy delivered, total amplitude of the stimulation, total volume of the stimulated tissue, a level of clinical response from the patient, a limit on one or more side effects (including, but not limited to, mood-related side effects that may be slower to occur), a limit on the volume or percentage of a side effect or avoidance region that is stimulated, a limit on the volume or percentage of the target that is stimulated, or the like or any combination thereof. Other examples of stimulation criteria include, but are not limited to, selecting monopolar stimulation (e.g., monopolar cathodic stimulation or monopolar anodic stimulation), bipolar stimulation, or any other specified multipolar stimulation arrangement; selecting a particular electrode or set of electrodes to be used for stimulation or eligible for use in stimulation; or the like or any combination thereof. In at least some embodiments, an estimated processing time or complexity of the search may be presented to the user. In at least some embodiments, the system may allow the user to elect to not proceed or may elect to adjust the inputs to reduce the processing time or complexity.

Figures 6, 7:
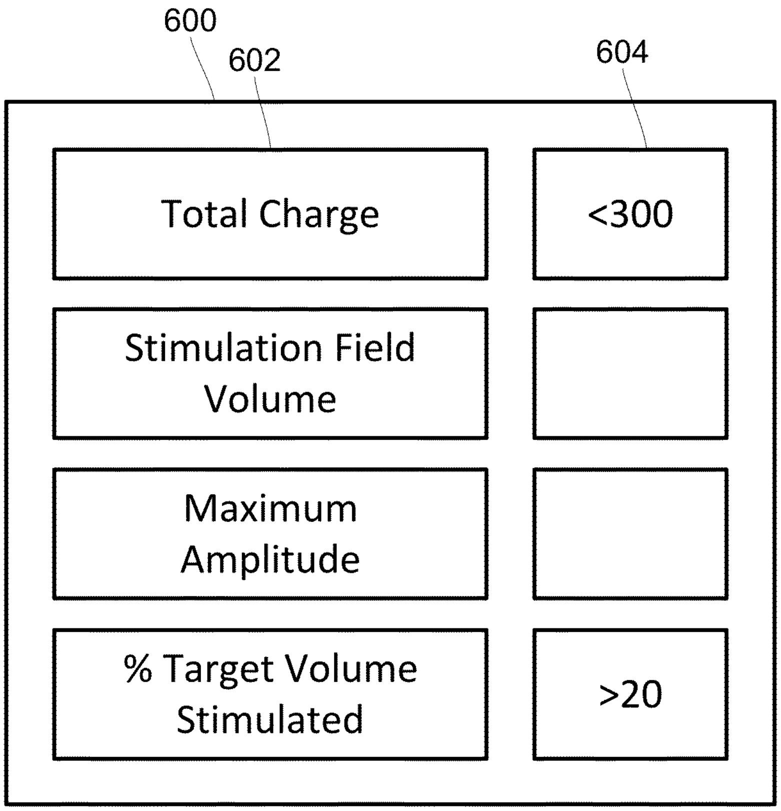
FIG. 6 is a schematic illustration of one embodiment of an interface for inputting stimulation criteria.
FIG. 7 is a chart including one example of values of a cost parameter, Background Ratio, obtained using the method of FIG. 5.

Any suitable mechanism can be used for selecting or specifying the stimulation criterion/criteria. In at least some embodiments, a system (or other programming arrangement) may display an interface that allows the user to input threshold values for one or more of the stimulation criterion/criteria. FIG. 6 illustrates one embodiment of an interface 600 with a list of stimulation criteria 602 (which may be selectable from a menu or other arrangement) and a space 604 for entry or selection of the threshold value (or other value or delineation) of the stimulation criterion.

In at least some embodiments, the user specifies whether a threshold value for a stimulation criterion is a maximum value or a minimum value. In at least some embodiments, the user may specify whether the threshold value is included in the acceptable range (for example, using the symbols ≥ or ≤) or is not included (for example, using the symbols > or <). It will be recognized, however, that, at least in some embodiments, the symbols > or < may be inclusive of the threshold value for ease of input (e.g., allowing input of values where the symbols ≥ or ≤ are not readily available on a keyboard or other input device.) In at least some embodiments, the user specifies threshold values as a range by setting a maximum value (which may or may not be within the range) and a minimum value (which may or may not be within the range).

Optionally, in step 504 values for one or more stimulation parameters (for example, pulse width, pulse frequency, or the like or any combination thereof) are received from the user. In at least some embodiments, the system may have default or preprogrammed values for one or more of the stimulation parameters and will use those default or preprogrammed values unless altered by a user. These values for stimulation parameter(s) may further limit the searching performed in the succeeding step. In at least some embodiments, specifying a value for one or more stimulation parameters that typically provide more limited variation in the stimulation may facilitate arriving at suitable programming parameters more quickly.

In step 506, the system (or other programming arrangement) identifies values (for example, “overlap values” as described in more detail below) of at least one cost parameter that correspond to a stimulation field that meets the stimulation criterion or all of the stimulation criteria, if there are more than one (optionally, limiting the search for a stimulation field by requiring the one or more stimulation parameters received from the user in step 504.)

In at least some embodiments, the user or the system selects one or more cost parameters for this step. In at least some embodiments, the cost parameter(s) for this step are predetermined by the system and, at least in some embodiments, the determination of the cost parameter(s) can be manually altered by a user.

In at least some embodiments, the system (or other programming arrangement) uses stimulation fields, as described above, to identify the values of the cost parameter(s) that meet the at least one stimulation criterion. An example of this is described below with respect to FIG. 7.

In step 508, the identified cost parameter values are provided to the user or to the electrical stimulation system (or other programming arrangement) or both. In at least some embodiments, the identified cost parameter values are displayed. In at least some embodiments, the display may also include values correspond to the stimulation criterion/criteria. One example of such a display is illustrated in FIG. 7 with values of a cost parameter, “Background Ratio,” being displayed along with the corresponding values for the two stimulation criteria, “Charge” and “% Target Volume Stimulated.” The display of the values of the cost parameter and, optionally, the corresponding values for the stimulation criterion/criteria may facilitate selection by the user of a value of the cost parameter.

In optional step 510, the system or a user selects one of the identified cost parameter values for input into the programming. System selection may include employing a metric, such as metric, m, above, to select a cost parameter value. Any other system-selection mechanism or procedure can be used.

In optional step 512, the IPG 14 is programmed using a set of stimulation parameters corresponding to the stimulation field represented by the selected cost parameter value. The patient can then be stimulated using this programmed set of stimulation parameters. In other embodiments, the user can continue programming the electrical stimulation system using the selected cost parameter value as an input or as a guide for modifications. It will be recognized that a user may or may not utilize the identified cost parameter values to program the IPG 14.

Figure 8:
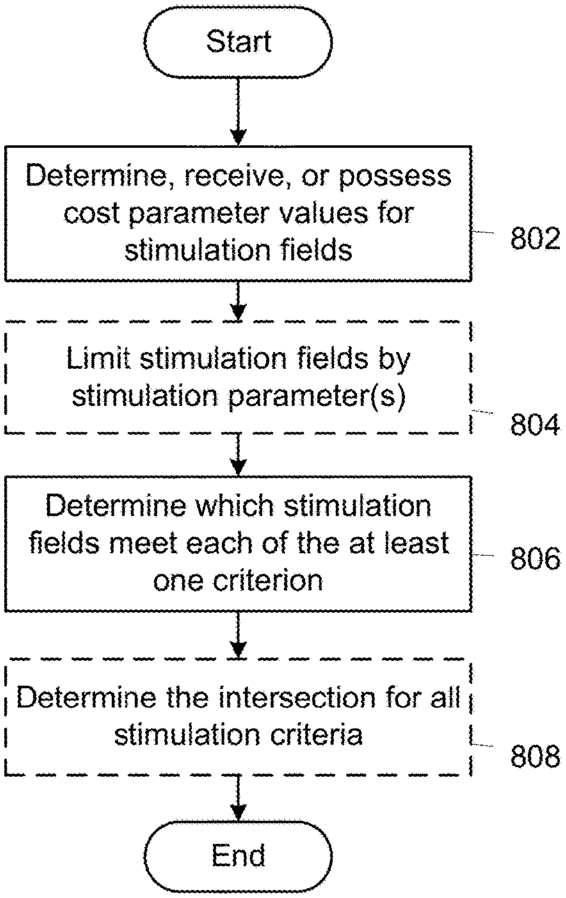
FIG. 8 is a flowchart of one embodiment of a method for identifying the values of a cost parameter.

As indicated above, the system (or other programming arrangement) identifies values of at least one cost parameter that meet the at least one stimulation criterion (optionally, limiting the search by requiring the one or more stimulation parameters received from the user in step 504.) FIG. 8 illustrates one embodiment of a method of identifying the values of the cost parameter(s) in step 506 of FIG. 5 above.

In step 802, the system (or other programming arrangement) determines, receives, or otherwise obtains or possesses the cost parameter values for multiple stimulation fields. Each stimulation field is defined by a particular set of stimulation parameters and represents an estimation of the volume of stimulation for the particular set of stimulation parameters.

In at least some embodiments, the stimulation fields are precalculated. In other embodiments, some or all of the stimulation fields can be calculated or interpolated from other calculated (or precalculated) stimulation fields during implementation of the method.

In at least some embodiments, the values for one or more cost parameters are precalculated for some or all of the stimulation fields are precalculated. In at least some embodiments, the values for one or more cost parameters are calculated for some or all of the stimulation fields during implementation of the method.

In optional step 804, the system (or other programming arrangement) limits the stimulation fields under consideration to those stimulation fields where the particular set of stimulation parameters that define the stimulation field includes the specific values for the one or more stimulation parameters received from the user in step 504. Only stimulation fields having the values for the stimulation parameter (s) received from the user are considered further. For example, if the user specifies a particular pulse width, only stimulation fields with that specific pulse width are considered further.

Figure 9A:
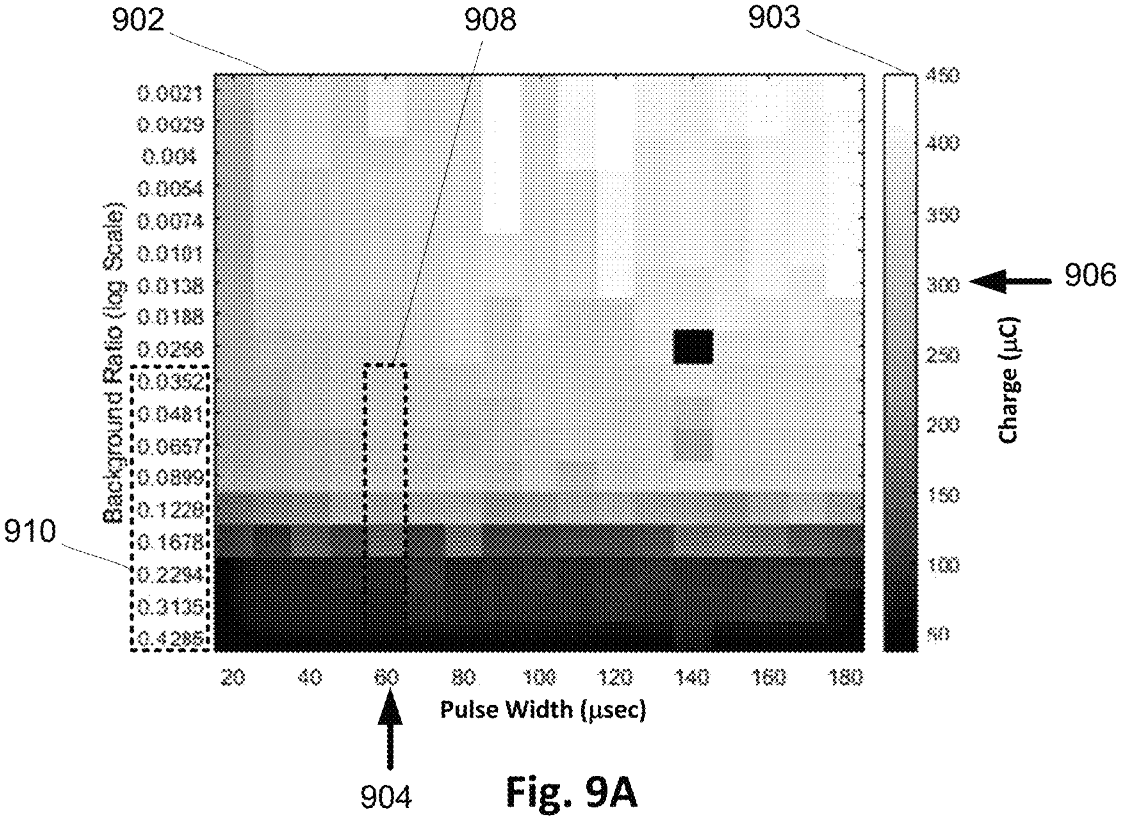
FIG. 9A is a graph of pulse width versus Background Ratio with shading (color in the original) corresponding to the value of the charge, in μC, to achieve that Background Ratio at the corresponding pulse width.
Figure 9B:
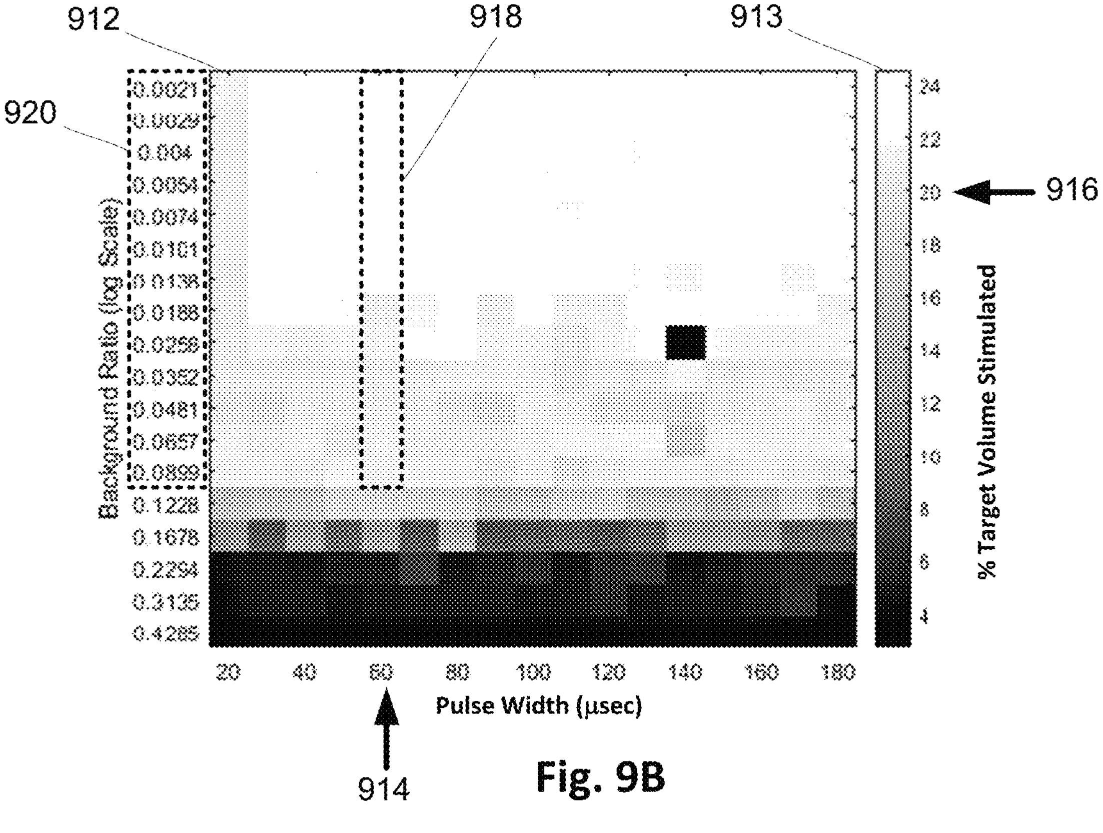
FIG. 9B is a graph of pulse width versus Background Ratio with shading (color in the original) corresponding to the value of the percentage (%) of a target volume that is stimulated to achieve that Background Ratio at the corresponding pulse width.

In step 806, for each of the at least one stimulation criterion, the system (or other programming arrangement) determines which of the stimulation fields under consideration, and the corresponding cost parameter values, meet that stimulation criterion. This step results in a set of cost parameter values (or stimulation fields) for each stimulation criterion that meet that stimulation criterion. FIGS. 9A and 9B illustrate step 806.

FIG. 9A is a graph 902 of pulse width versus Background Ratio with shading (color in the original) corresponding to the value of the charge, in to achieve that Background Ratio at the corresponding pulse width. Each of the shaded regions corresponds to a stimulation field having the indicated charge, pulse width, and Background Ratio. The index 903 indicates the degree of shading for each of the indicated values of the charge with larger charge having a lighter shading. For FIG. 9A, a user has specified a value 904 for the pulse width of 60 μsec and has specified a stimulation criterion 906 of a charge no more than 300 μC. The box 908 captures entries that have the value 904 and meet the stimulation criterion 906. The box 910 captures the corresponding values of the Background Ratio.

FIG. 9B is a graph 912 of pulse width versus Background Ratio with shading (color in the original) corresponding to the value of the percentage (%) of a target volume that is stimulated to achieve that Background Ratio at the corresponding pulse width. Each of the shaded regions corresponds to a stimulation field having the indicated percentage of the target volume that is stimulated, pulse width, and Background Ratio. The index 903 indicates the degree of shading for each of the indicated percentage of the target volume that is stimulated with higher values being lighter. For FIG. 9B, a user has specified a value 914 for the pulse width of 60 μsec and has specified a stimulation criterion 916 of at least 20% of the target volume is stimulated. The box 918 captures entries that have the value 914 and meet the stimulation criterion 916. The box 920 captures the corresponding values of the Background Ratio.

In optional step 808, when two or more stimulation criteria have been received, the system (or other programming arrangement) determines the overlap (e.g., intersection) of the sets of cost parameter values (or stimulation fields) for all of the stimulation criteria. This overlap typically results in identifying one or more overlap values (i.e., cost parameter values) that correspond to stimulation fields that meet all of the stimulation criteria. For example, the values of the Background Ratio in FIG. 7 correspond to overlap values for box 910 of FIG. 9A and box 920 of FIG. 9B.

When the overlap between the sets of cost parameter values for the stimulation criteria is empty, none of the stimulation fields meet all of the stimulation criteria and, therefore, there is no overlap value. In at least some embodiments, the system (or other programming arrangement) provides a message to the user that the two or more stimulation criteria have not been met. In at least some embodiments, this message may prompt the user to modify the stimulation criteria, selected values for the stimulation parameter(s), or any combination thereof so that overlap value(s) may be found using the modified inputs. In at least some embodiments, the message may provide cost parameter values that meet at least one (or some, but not all) of the stimulation criteria.

In at least some embodiments, the system (or other programming arrangement) can implement a search procedure to test a set of cost parameter/stimulation parameter values, stimulate the patient, capture a response to the stimulation, and identify a next set of cost parameter/stimulation parameter values to test. In at least some embodiments, the search procedure can continue until convergence is obtained or the user or system stops the procedure.

Figure 10:
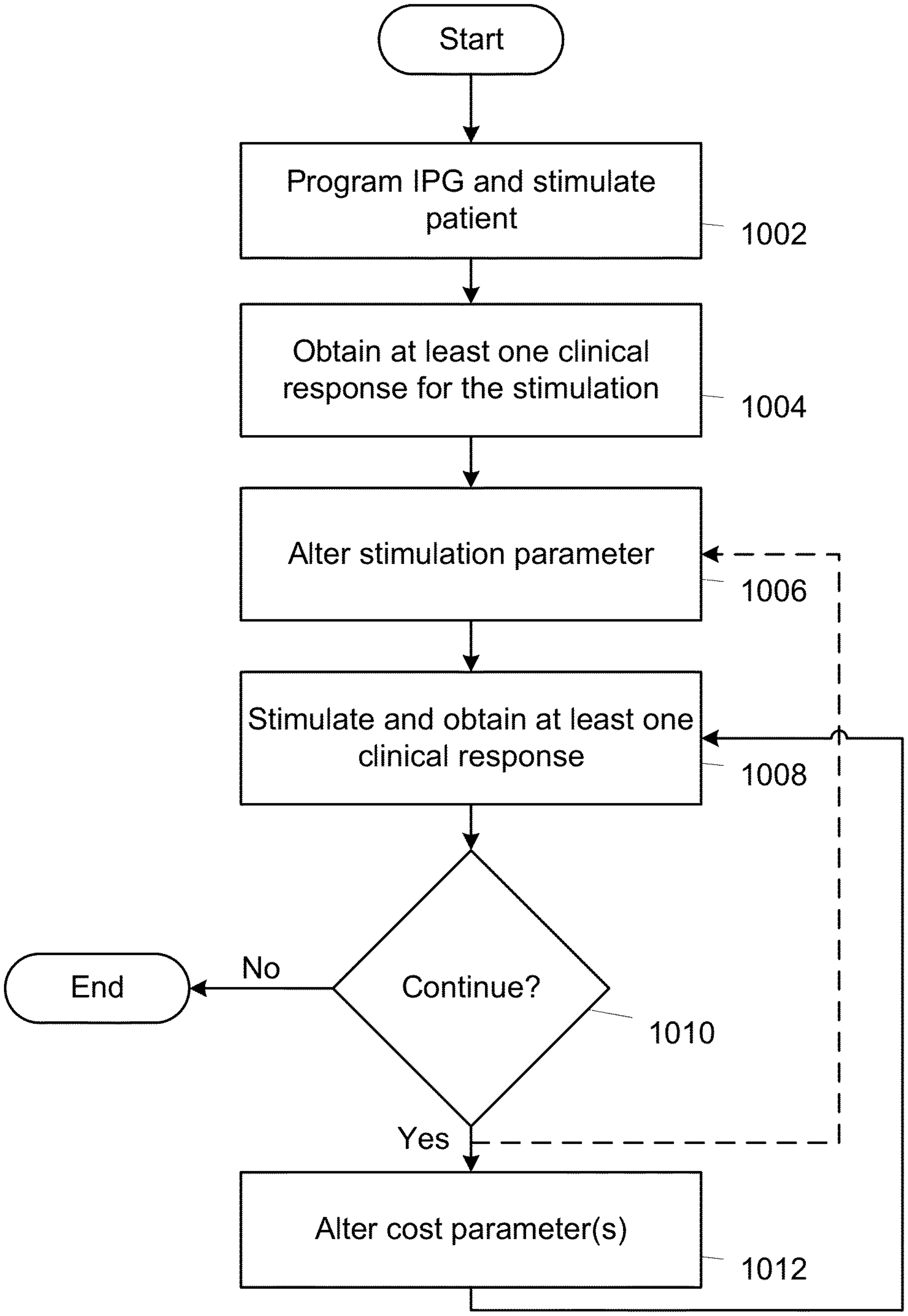
FIG. 10 is a flowchart of one embodiment of a method for iteratively searching for stimulation parameters.

FIG. 10 illustrates one method of iteratively searching for stimulation parameters. In step 1002, the system or user can program the IPG with the stimulation field corresponding to one or more cost parameter values obtained as described above. Then the IPG can stimulate a patient using the programming.

In step 1004, at least one clinical response is obtained for the stimulation. The observation, determination, or input of the clinical response may be performed by the user, the patient, or any other suitable person or the clinical response can be observed or determined by a processor of the system or a sensor or other device. Examples of clinical responses include, but are not limited to, manually assessed clinical scores, sensor-derived scores or values, electrophysiological signals, or the like or any combination thereof. For example, a user may input a quantitative or qualitative indication based on visual observation of the patient, a sensor, or data (for example, an EEG or ECG or the like); verbal feedback from the patient; an evoked compound action potential (ECAP) or an evoked resonant neural activity (ERNA)); local field potentials (LFP); or the like. As another example, at least one sensor (for example, a haptic sensor, accelerometer, gyroscope, EEG, EMG, camera, or the like) may be used to observe or determine a clinical response and may provide a quantitative or qualitative value (either directly to the processor or through a programmer, a user, the patient, or another person) that indicates a clinical response. A quantitative or qualitative value can indicate, for example, at least one characteristic of a symptom (for example, tremor), a therapeutic effect or side effect (for example, change in the patient's balance), electrical activity, or the like. The clinical response may be indicative of a therapeutic effect or a side effect or both. Moreover, in at least some embodiments, more than one clinical response can be observed, determined, or input for each stimulation instance.

In step 1006, a stimulation parameter is altered. For example, the stimulation amplitude is increase.

In step 1008, the patient is stimulated with the new set of stimulation parameters, and the clinical response is obtained. For example, the stimulation amplitude is increased and the system/user determine what therapeutic benefit(s), side effect(s), or any combination thereof are obtained at the new stimulation amplitude. The user would then increase amplitude and record what benefits and side effects are observed.

In step 1010, a query can be made whether to continue the procedure. For example, the query may determine if the clinical response indicates a benefit with no side effects (or with side effects below a threshold value) and a goal (for example, a target score) for each of one or more desired benefits has been met. If yes, then the procedure can be halted. In at least some embodiments, a set of parameters that provides the highest score for each desired benefit (or an accumulated highest score for multiple benefits) will be selected for use.

If the query in step 1008 has a "no" result, then, in step 1012, one or more cost parameters may be altered based on the clinical response in step 1008. For example, when the clinical response indicates a side effect above a threshold level (which may be a level of "no side effect" or some other specified level of side effect), then an avoidance cost parameter is set at higher avoidance or a background ratio would be set at lower spill into non-target regions. When the clinical response indicates a benefit with no side effects (or with side effects below a threshold value) but the target score for each desired benefit has not been met, then an avoidance cost parameter is set at lower avoidance, a background ratio is set at higher spill into non-target regions, or any combination thereof.

The procedure returns to step 1008 and continues until the query in step 1010 is "yes" or the procedure is terminated by a user or the system. As an alternative, after one or more queries in step 1008 with a "yes" result, the procedure can return to step 1006 and alter a stimulation parameter instead of altering a cost parameter (step 1012). This would allow the procedure to investigate a stimulation parameter space as well as a cost parameter space.

Figure 11:
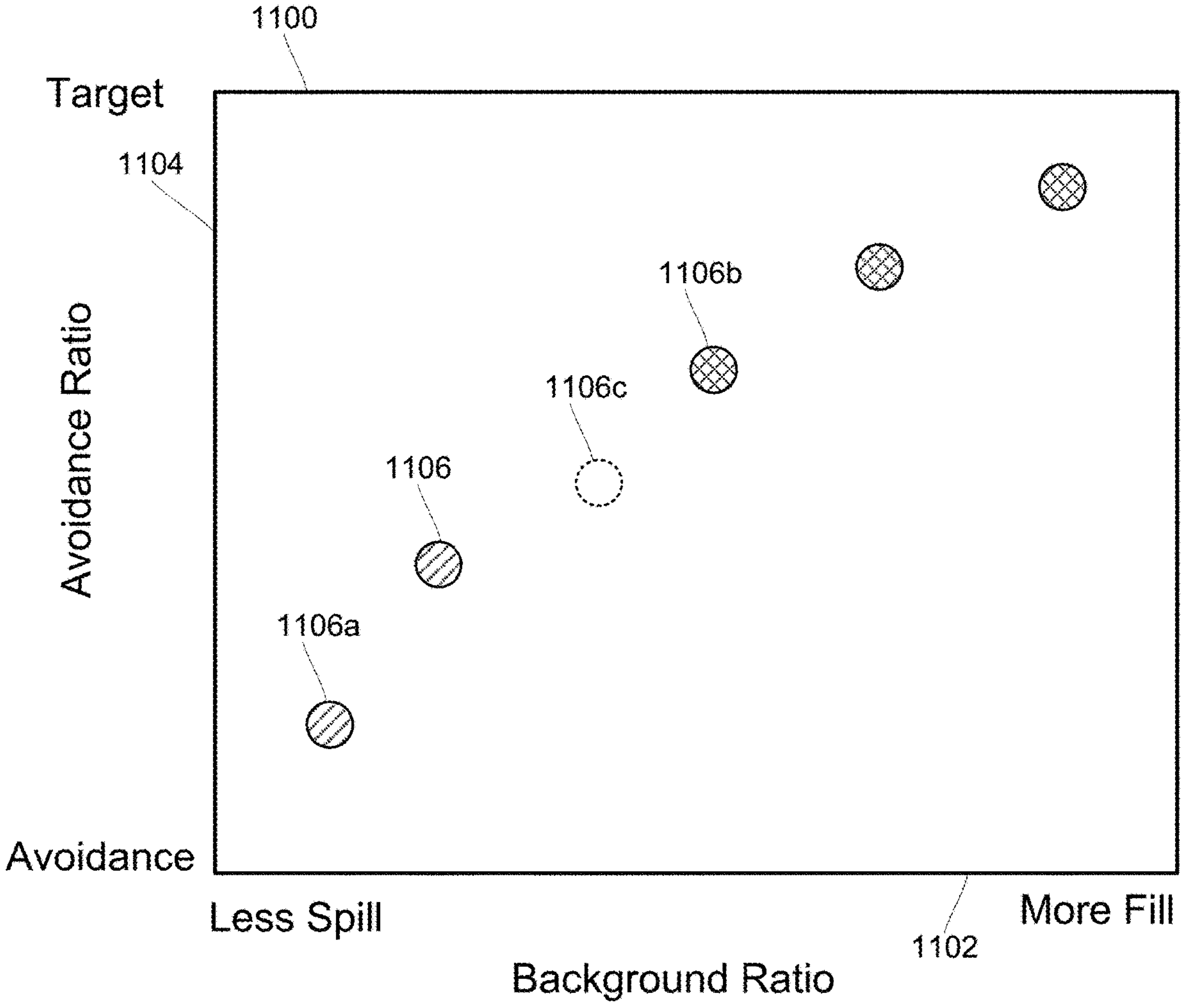
FIG. 11 is one embodiment of a map of clinical effects obtained for different combinations of values of Background Ratio and Avoidance Ratio.

In at least some embodiments, a map 1100 can be presented, as illustrated in FIG. 11. The map 1100 has one axis 1102 representing the Background Ratio (ranging from, for example, "less spill" outside the target to "more fill" of the target) and another axis 1104 representing the Avoidance Ratio (ranging from "avoidance" to avoid side effect and avoidance regions to "target" for increasing the volume of the target that is stimulated). Clinical responses for tested stimulations are indicated by dots 1106 where the dots **1106*a* have a beneficial therapeutic effect without side effects (or with side effects below a threshold value) and dots 1106*b*** that have both beneficial therapeutic effects and side effects. It will be recognized that other dots could have a) no therapeutic effect or side effects or b) no therapeutic effect but include side effects. The different types of dots could be differentiated graphically using color, shading, crosshatching, or the like or any combination thereof.

Each dot 1106 is graphed on the map 1100 at a particular combination of values of Background Ratio and Avoidance Ratio. In at least some embodiments, a system or method can propose a new combination of values, such as that represented by dot 1106*c* based on the previously tested combinations. In at least some embodiments, identification of a side effect would suggest that the next combination of values should be down, to the left, or a combination of down and left of the current combination. A combination with no side effects would suggest that the next combination of values should be up, to the right, or a combination of up and right of the current combination.

Examples of other clinical response (or clinical effects) maps that could be adapted to map 1100 are described in U.S. Pat. No. 10,071,249; U.S. Patent Application Publication No. 2014/0277284; and U.S. Provisional Patent Application Ser. No. 63/288,153, all of which are incorporated herein by reference in their entireties.

It will be understood that each block of the flowchart illustrations, and combinations of blocks in the flowchart illustrations and methods disclosed herein, can be implemented by computer program instructions. These program instructions may be provided to a processor to produce a machine, such that the instructions, which execute on the processor, create means for implementing the actions specified in the flowchart block or blocks disclosed herein. The computer program instructions may be executed by a processor to cause a series of operational steps to be performed by the processor to produce a computer implemented process. The computer program instructions may also cause at least some of the operational steps to be performed in parallel. Moreover, some of the steps may also be performed across more than one processor, such as might arise in a multi-processor computer system. In addition, at least one process may also be performed concurrently with other processes, or even in a different sequence than illustrated without departing from the scope or spirit of the invention.

The computer program instructions can be stored on any suitable computer-readable medium including, but not limited to, RAM, ROM, EEPROM, flash memory or other memory technology, CD-ROM, digital versatile disks ("DVD") or other optical storage, magnetic cassettes, magnetic tape, magnetic disk storage or other magnetic storage devices, in the cloud or other non-local site, or any other medium which can be used to store the desired information and which can be accessed by a computing device.

A system can include one or more processors that can perform the methods (in whole or in part) described above. In at least some embodiments, some or all of the method may be performed using one or more non-local processor(s) (for example, processors in another device or in the cloud.) The methods, systems, and units described herein may be embodied in many different forms and should not be construed as limited to the embodiments set forth herein. Accordingly, the methods, systems, and units described herein may take the form of an entirely hardware embodiment, an entirely software embodiment or an embodiment combining software and hardware aspects. The methods described herein can be performed using any type of processor or any combination of processors where each processor performs at least part of the process. In at least some embodiments, the processor may include more than one processor.

The above specification provides a description of the structure, manufacture, and use of the invention. Since many embodiments of the invention can be made without departing from the spirit and scope of the invention, the invention also resides in the claims hereinafter appended.

What is claimed as new and desired to be protected by Letters Patent of the United States is:

1. A method for programming an electrical stimulation system comprising at least one implantable electrical stimulation lead comprising a plurality of electrodes, the method comprising:

receiving a target and a location of the at least one implantable electrical stimulation lead;

receiving at least one stimulation criterion;

for each of the at least one stimulation criterion, a) for each of at least one value of a cost parameter, calculating the value of the cost parameter by 1) determining a cost of stimulating at least one defined region of tissue, 2) determining a benefit of stimulating a region of the target, and 3) calculating the value of the cost parameter as a ratio of the cost of stimulating the at least one defined region of tissue over the benefit of stimulating the region of the target, and b) identifying one or more values of the cost parameter that meet the at least one stimulation criterion;

programming the electrical stimulation system utilizing a one of the one or more values of the cost parameter that meet the at least one stimulation criterion; and stimulating a patient using the at least one implantable electrical stimulation lead and the programming of the electrical stimulation system utilizing the one of the one or more values of the cost parameter that meet the at least one stimulation criterion.

2. The method of claim 1, wherein the at least one stimulation criterion is at least two stimulation criteria, the method further comprising identifying, from the identified one or more values of the cost parameter, at least one overlap value of the cost parameter that meets each of the at least two stimulation criterion, and providing the at least one overlap value to a user or the electrical stimulation system to assist in programming the electrical stimulation system.

3. The method of claim 2, further comprising providing a message to a user or the electrical stimulation system when no overlap value is identified.

4. The method of claim 1, further comprising receiving a user selection of a one of the one or more values of the cost parameter that meet the at least one stimulation criterion.

5. The method of claim 1, wherein the cost of stimulating the at least one defined region of tissue is either a) a cost of stimulating a volume of tissue around the at least one implantable electrical stimulation lead; b) a cost of stimulating a volume of tissue outside of the at least one defined region of tissue; or c) a cost of stimulating a volume of a side effect or avoidance region.

6. The method of claim 1, further comprising receiving at least one side effect or avoidance region.

7. The method of claim 1, wherein the identifying the one or more values of the cost parameter comprises, for each of the at least one stimulation criterion, comparing a plurality of stimulation fields to the at least one stimulation criterion and determining which of the stimulation fields meet the at least one stimulation criterion, wherein each of the stimulation fields corresponds to an estimated volume of stimulation for a particular set of stimulation parameters corresponding the stimulation field, wherein each of the stimulation fields has a value of the cost parameter determined from the estimated volume of stimulation for the particular set of stimulation parameters.

8. The method of claim 1, further comprising
obtaining at least one clinical response for the stimulation;
altering a stimulation parameter;
performing a second stimulation of the patient using the altered stimulation parameter;
obtaining at least one clinical response for the second stimulation; and
querying whether the at least one clinical response for the second stimulation meets a goal for each of one or more desired benefits without generating a side effect above a threshold value.

9. The method of claim 8, further comprising
when a result of the querying is negative,
i) altering the one of the one or more values of the cost parameter that meet the at least one stimulation criterion to provide an altered value of the cost parameter;
ii) programming the electrical stimulation system utilizing the altered value of the cost parameter;
iii) performing a third stimulation of the patient using the at least one implantable electrical stimulation lead and the programming of the electrical stimulation system utilizing the altered value of the cost parameter;
iv) obtaining at least one clinical response for the third stimulation;
v) querying whether the at least one clinical response for the third stimulation meets a target for each of one or more desired benefits without generating a side effect above a threshold value; and
repeating steps i)-v) when a result of the querying in step v) is negative.

10. The method of claim 9, further comprising forming a map of the at least one clinical response for each of the first stimulation, the second stimulation, and each instance of the third stimulation, wherein the map has a first axis corresponding the cost parameter and a second axis corresponding to a second cost parameter.

11. An electrical stimulation system, comprising:
at least one implantable electrical stimulation lead comprising a plurality of electrodes;
a control unit coupled to the at least one implantable electrical stimulation lead and configured for generating electrical stimulation for delivery through the at least one implantable electrical stimulation lead; and
a processor configured to identify stimulation parameters for programming of the control unit to generate the electrical stimulation, the processor configured to perform actions comprising:
receiving a target and a location of the at least one implantable electrical stimulation lead;
receiving at least one stimulation criterion;
for each of the at least one stimulation criterion,
a) for each of at least one value of a cost parameter, calculating the value of the cost parameter by
1) determining a cost of stimulating at least one defined region of tissue,
2) determining a benefit of stimulating a region of the target, and
3) calculating the value of the cost parameter as a ratio of the cost of stimulating the at least one defined region of tissue over the benefit of stimulating the region of the target, and
b) identifying one or more values of the cost parameter that meet the at least one stimulation criterion;
programming the electrical stimulation system utilizing a one of the one or more values of the cost parameter that meet the at least one stimulation criterion; and
stimulating a patient using the at least one implantable electrical stimulation lead and the programming of the electrical stimulation system utilizing the one of the one or more values of the cost parameter that meet the at least one stimulation criterion.

12. The electrical stimulation system of claim 11, wherein the cost of stimulating at least one defined region of tissue is either a) a cost of stimulating a volume of tissue around the at least one implantable electrical stimulation lead; b) a cost of stimulating a volume of tissue outside of the at least one defined region of tissue; or c) a cost of stimulating a volume of a side effect or avoidance region.

13. The electrical stimulation system of claim 11, wherein the at least one stimulation criterion is at least two stimulation criteria,
the actions further comprising identifying, from the identified one or more values of the cost parameter, at least one overlap value of the cost parameter that meets each of the at least two stimulation criterion, and
providing the at least one overlap value to a user or the electrical stimulation system to assist in programming the electrical stimulation system.

14. The electrical stimulation system of claim 11, wherein the actions further comprise
obtaining at least one clinical response for the stimulation;
altering a stimulation parameter;
performing a second stimulation of the patient using the altered stimulation parameter;
obtaining at least one clinical response for the second stimulation; and
querying whether the at least one clinical response for the second stimulation meets a goal for each of one or more desired benefits without generating a side effect above a threshold value.

15. The electrical stimulation system of claim 14, wherein the actions further comprise
when a result of the querying is negative,
i) altering the one of the one or more values of the cost parameter that meet the at least one stimulation criterion to provide an altered value of the cost parameter;
ii) programming the electrical stimulation system utilizing the altered value of the cost parameter;
iii) performing a third stimulation of the patient using the at least one implantable electrical stimulation lead and the programming of the electrical stimulation system utilizing the altered value of the cost parameter;
iv) obtaining at least one clinical response for the third stimulation;
v) querying whether the at least one clinical response for the third stimulation meets a target for each of one or more desired benefits without generating a side effect above a threshold value; and
repeating steps i)-v) when a result of the querying in step v) is negative.

16. The electrical stimulation system of claim 15, wherein the actions further comprise forming a map of the at least one clinical response for each of the first stimulation, the second stimulation, and each instance of the third stimulation, wherein the map has a first axis corresponding the cost parameter and a second axis corresponding to a second cost parameter.

17. The electrical stimulation system of claim 11, wherein the identifying the one or more values of the cost parameter comprises, for each of the at least one stimulation criterion, comparing a plurality of stimulation fields to the at least one stimulation criterion and determining which of the stimulation fields meet the at least one stimulation criterion, wherein each of the stimulation fields corresponds to an estimated volume of stimulation for a particular set of stimulation parameters corresponding the stimulation field, wherein each of the stimulation fields has a value of the cost parameter determined from the estimated volume of stimulation for the particular set of stimulation parameters.

18. A non-transitory computer-readable medium having computer executable instructions stored thereon that, when executed by at least one processor, cause the at least one processor to perform actions comprising:

receiving a target and a location of the at least one implantable electrical stimulation lead;

receiving at least one stimulation criterion;

for each of the at least one stimulation criterion, a) for each of at least one value of a cost parameter, calculating the value of the cost parameter by 1) determining a cost of stimulating at least one defined region of tissue, 2) determining a benefit of stimulating a region of the target, and 3) calculating the value of the cost parameter as a ratio of the cost of stimulating the at least one defined region of tissue over the benefit of stimulating the region of the target, and b) identifying one or more values of the cost parameter that meet the at least one stimulation criterion;

programming the electrical stimulation system utilizing a one of the one or more values of the cost parameter that meet the at least one stimulation criterion; and stimulating a patient using the at least one implantable electrical stimulation lead and the programming of the electrical stimulation system utilizing the one of the one or more values of the cost parameter that meet the at least one stimulation criterion.

19. The non-transitory computer-readable medium of claim 18, wherein the cost of stimulating at least one defined region of tissue is either a) a cost of stimulating a volume of tissue around the at least one implantable electrical stimulation lead; b) a cost of stimulating a volume of tissue outside of the at least one defined region of tissue; or c) a cost of stimulating a volume of a side effect or avoidance region.

20. The non-transitory computer-readable medium of claim 18, wherein the at least one stimulation criterion is at least two stimulation criteria, the actions further comprising identifying, from the identified one or more values of the cost parameter, at least one overlap value of the cost parameter that meets each of the at least two stimulation criterion, and providing the at least one overlap value to a user or the electrical stimulation system to assist in programming the electrical stimulation system.

* * * * *